United States Patent [19]
Chu

[11] Patent Number: 5,958,341
[45] Date of Patent: Sep. 28, 1999

[54] APPARATUS FOR EFFICIENT PROCESSING OF TISSUE SAMPLES ON SLIDES

[75] Inventor: Wei-Sing Chu, Silver Spring, Md.

[73] Assignee: American Registry of Pathology, Washington, D.C.

[21] Appl. No.: 08/780,029

[22] Filed: Dec. 23, 1996

[51] Int. Cl.$^6$ ................................................. B01L 11/00
[52] U.S. Cl. ........................... 422/99; 422/100; 422/102; 422/104; 422/63
[58] Field of Search ................................ 422/99–104, 63

[56] References Cited

U.S. PATENT DOCUMENTS

| | | |
|---|---|---|
| 4,336,765 | 6/1982 | Coughlin ................................... 118/50 |
| 4,347,750 | 9/1982 | Tersteeg et al. ...................... 73/864.31 |
| 4,595,561 | 6/1986 | Thornton et al. ......................... 422/58 |
| 4,731,335 | 3/1988 | Brigati .................................... 436/180 |
| 4,777,020 | 10/1988 | Brigati . |
| 4,798,706 | 1/1989 | Brigati .................................... 422/102 |
| 4,800,159 | 1/1989 | Mullis et al. . |
| 4,801,431 | 1/1989 | Cuomo et al. . |
| 4,975,250 | 12/1990 | Mordecki . |
| 4,985,206 | 1/1991 | Bowman et al. . |
| 5,002,736 | 3/1991 | Babbitt et al. . |
| 5,021,218 | 6/1991 | Davis et al. ............................. 422/104 |
| 5,023,187 | 6/1991 | Koebler et al. . |
| 5,192,503 | 3/1993 | McGrath et al. . |
| 5,269,918 | 12/1993 | Lapidus et al. ......................... 210/232 |
| 5,318,749 | 6/1994 | Eberle ....................................... 422/72 |
| 5,364,790 | 11/1994 | Atwood et al. . |
| 5,439,649 | 8/1995 | Tseung et al. ............................. 422/99 |

OTHER PUBLICATIONS

Description of Dakostainer Universal Staining System (one page).
Description of SlideMaster from Lab Vision Corporation (two pages).
Description of Stainplate™ Staining Accelerator from Signet Laboratories, Inc. (one page).
Description of the Ventana ES IHC Staining System (3 pages).
Description of the Shandon Lipshaw Cadenza® Automated Immunostainer (5 pages).
D. Brigati et al. (1988). "Immunocytochemistry is Automated: Development of A Robotic Workstation Based Upon the Capillary Action Principle," *J. Histotechnology* 11:165–183.
C.M. McGrath et al. (1995). "Influence of Surface:Volume Ratio of Reaction Chambers on Stoichiometry of Antibody-–Based Reactions In Situ," *Cell Vision* 2:165–169.
G.J. Nuovo (1994). "In Situ Detection of PCR–amplified DNA and cDNA: A Review" *J. Histotechnology* 17:235, 240–242.

*Primary Examiner*—Harold Y. Pyon
*Attorney, Agent, or Firm*—Rothwell, Figg, Ernst & Kurz, P.C.

[57] ABSTRACT

Slideholders which are useful for manually processing tissue samples on microscope slides are described. These slideholders hold multiple slides and are designed in conjunction with specialized trays for rapidly processing the mounted tissue samples such as for immunocytochemical staining. The slideholder plus tray assemblies incorporate several useful advantages including a requirement for minimal reaction fluid volumes, ease of handling several slides concurrently, prevention of evaporation of reaction fluids, protection of the tissue from extraneous environmental contamination, and the ability to perform in situ PCR. Various aspects of the design aid in removing trapped air from the reaction fluids and in adding fluids to the tissue sample. One embodiment comprises a coverslip with a soft top which aids in prevention of tissue degradation by preventing pressure buildup during PCR. The system results in very low background signals and allows for manually processing manifold times the number of slides as is typically possible with other current manual methods.

18 Claims, 20 Drawing Sheets

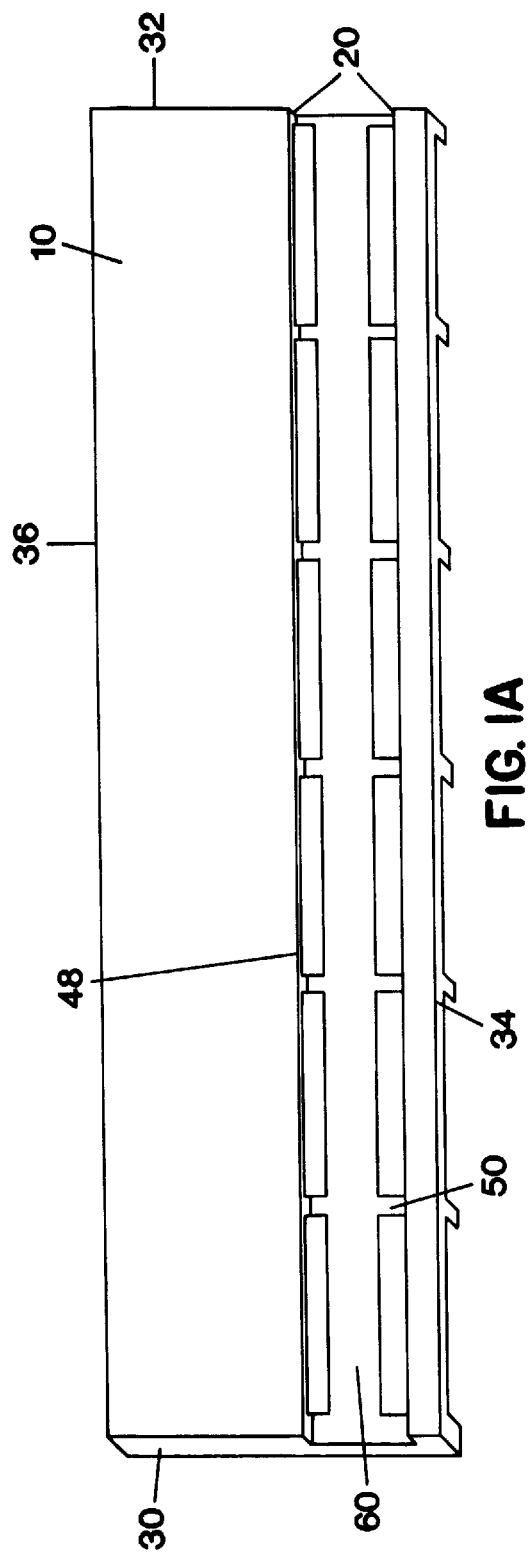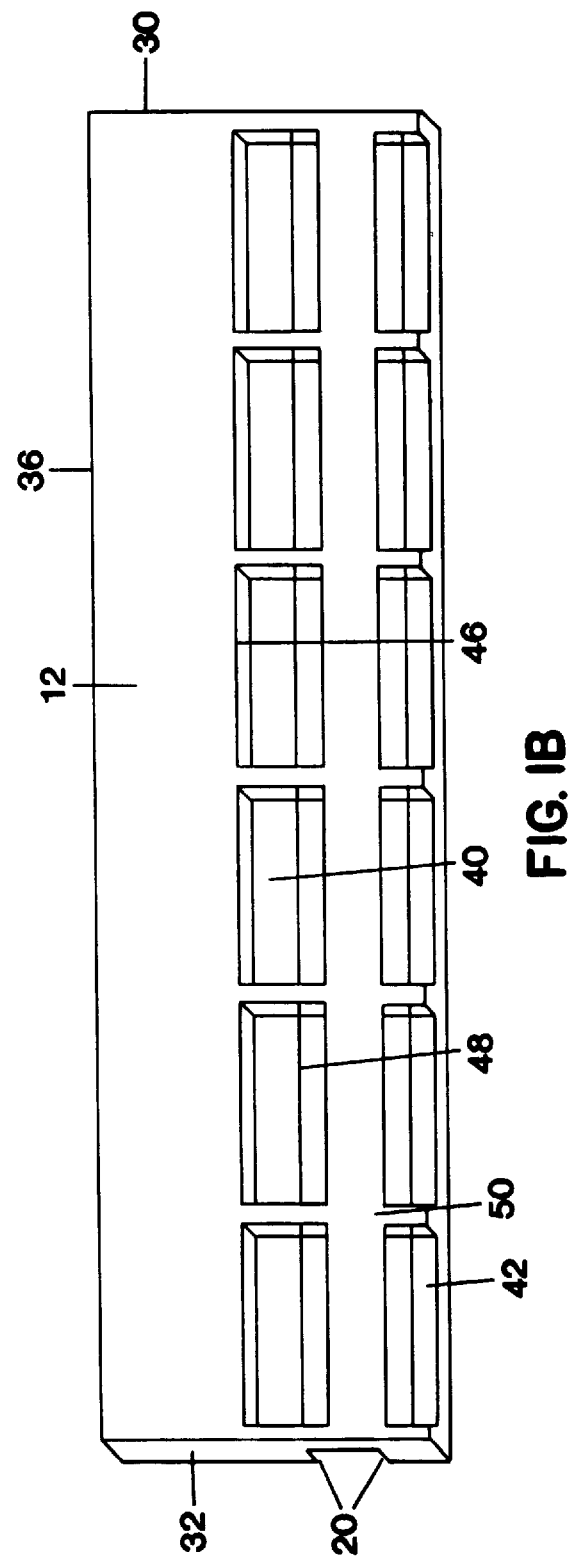
FIG. 1A
FIG. 1B

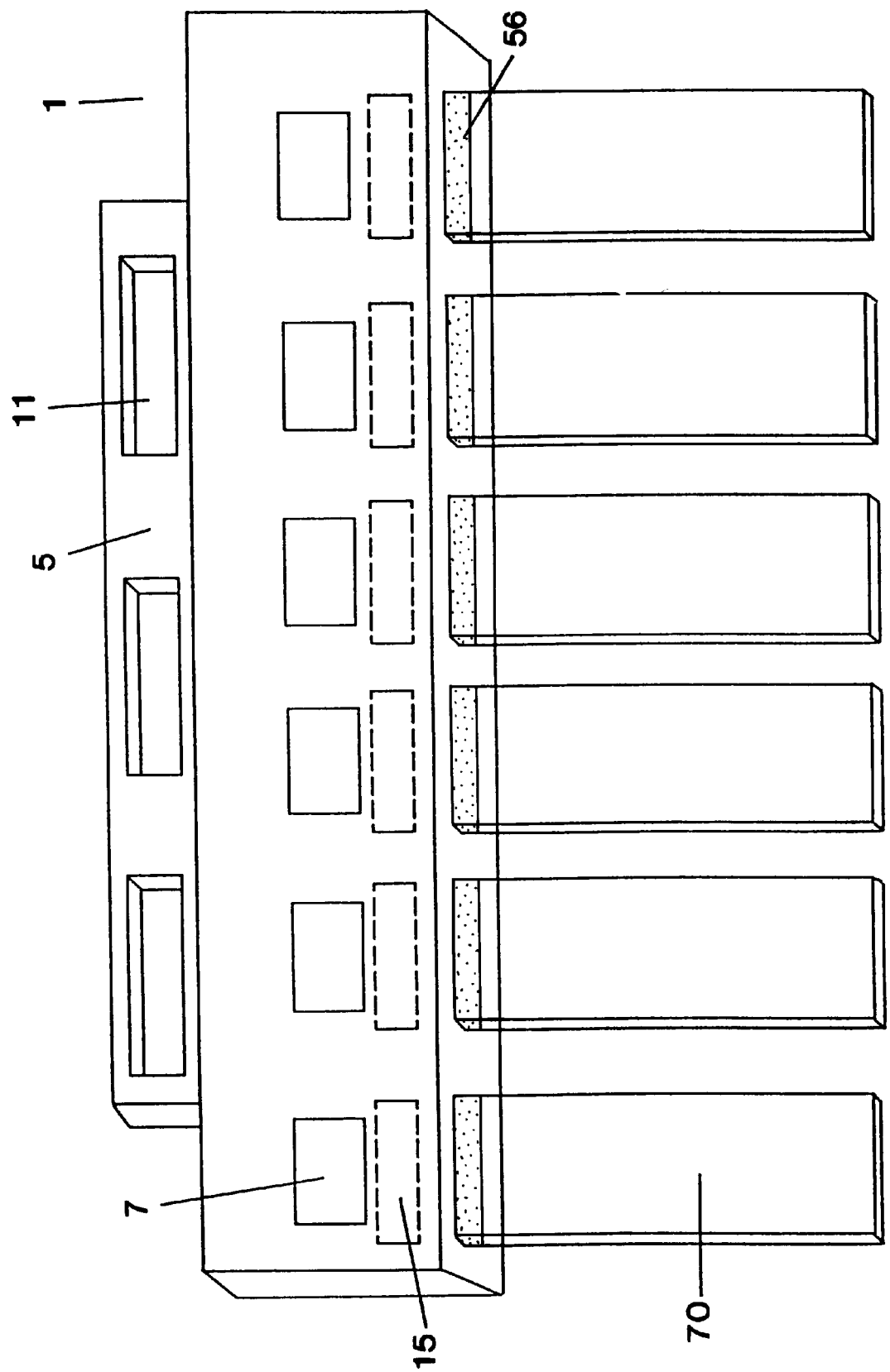
FIG. IE

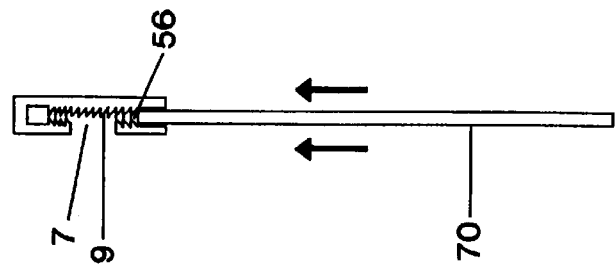
FIG. IG
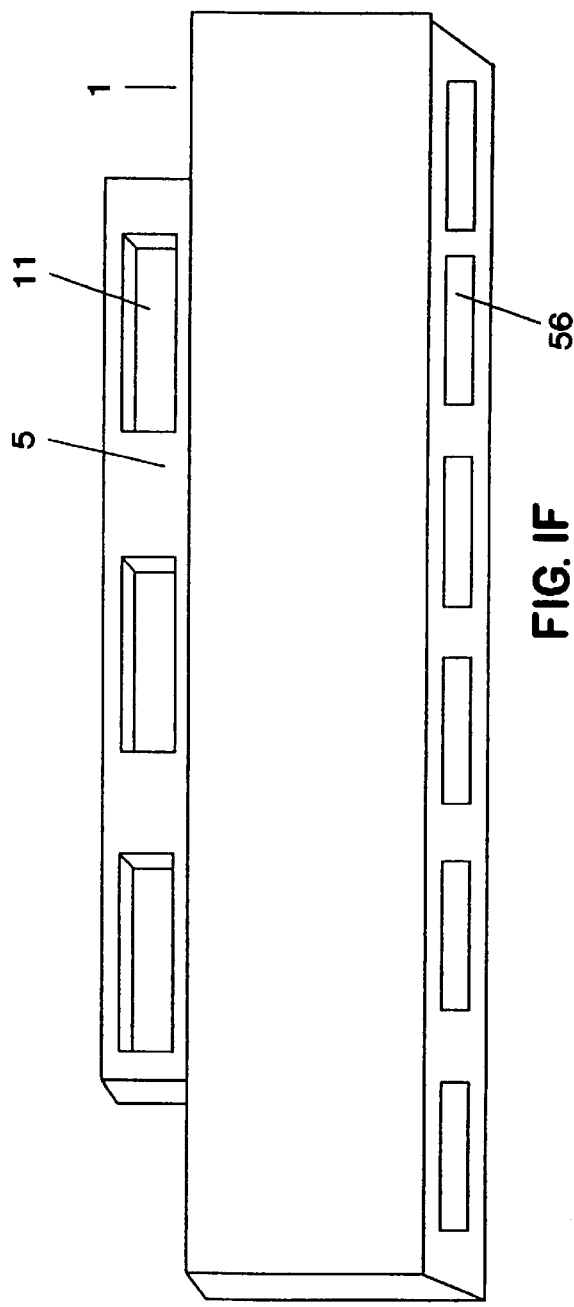
FIG. IF

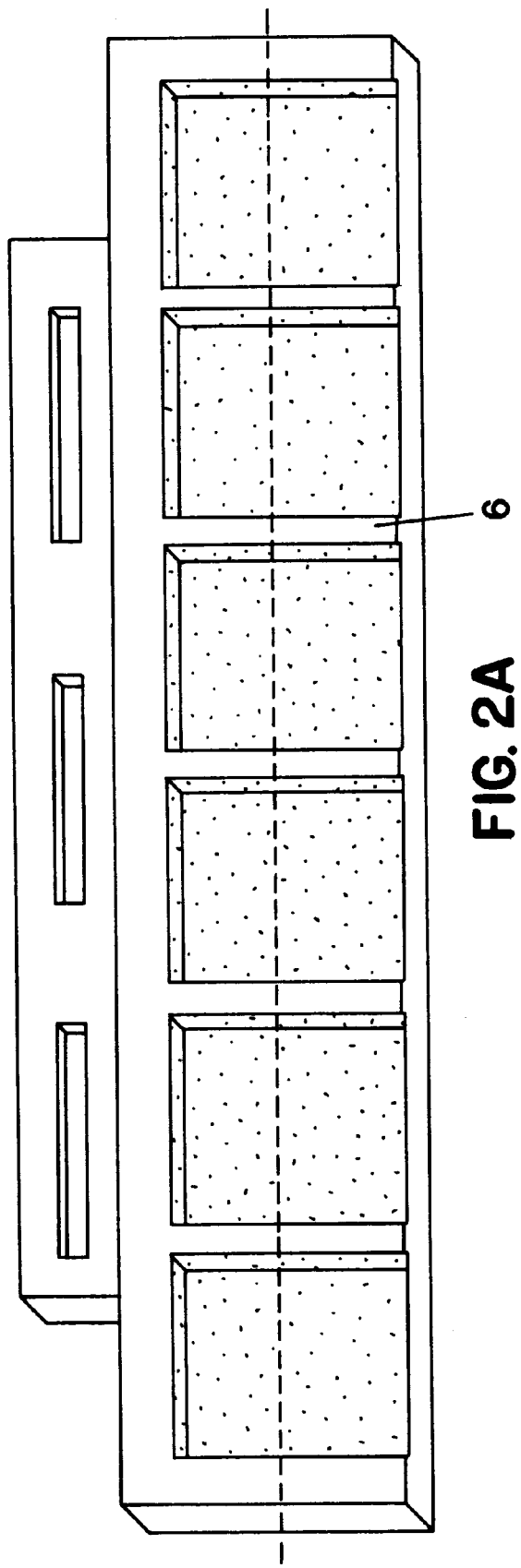
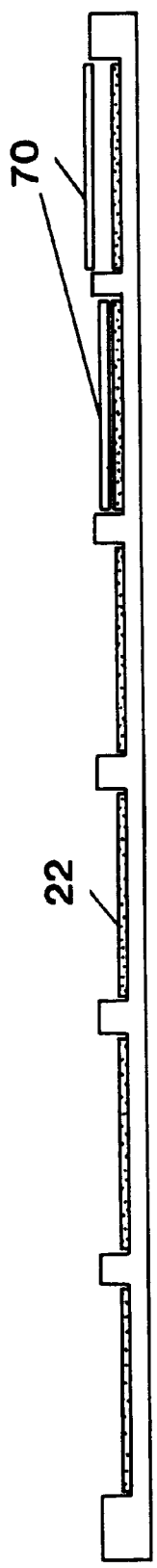
FIG. 2A
FIG. 2B

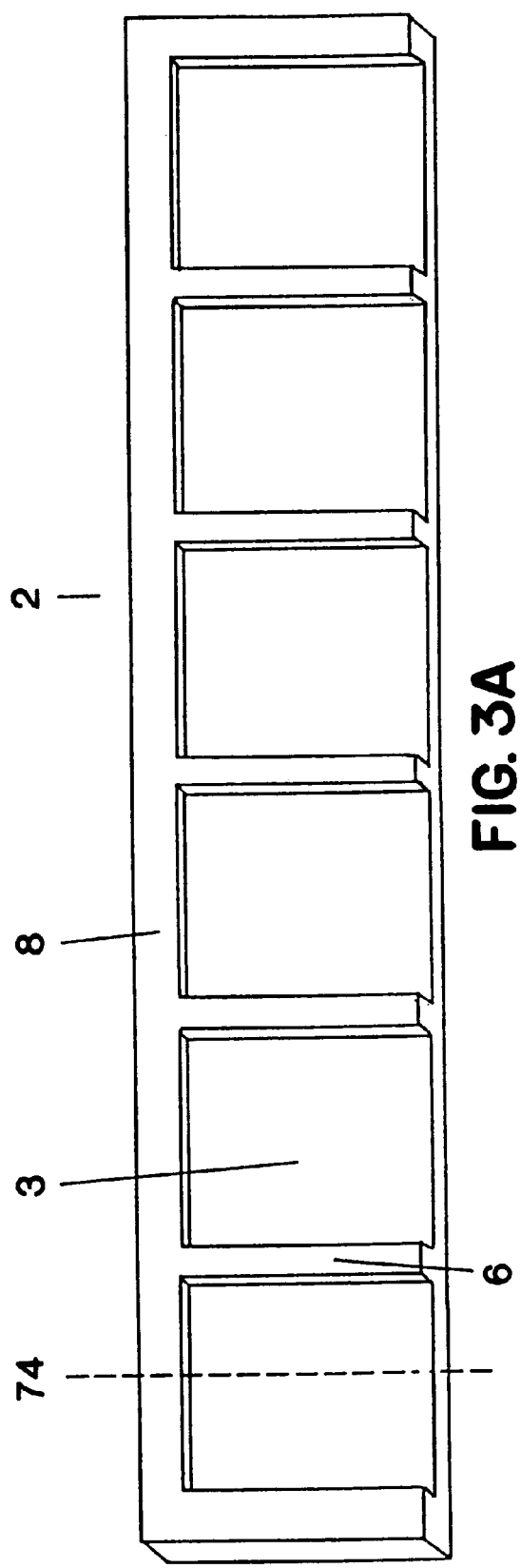
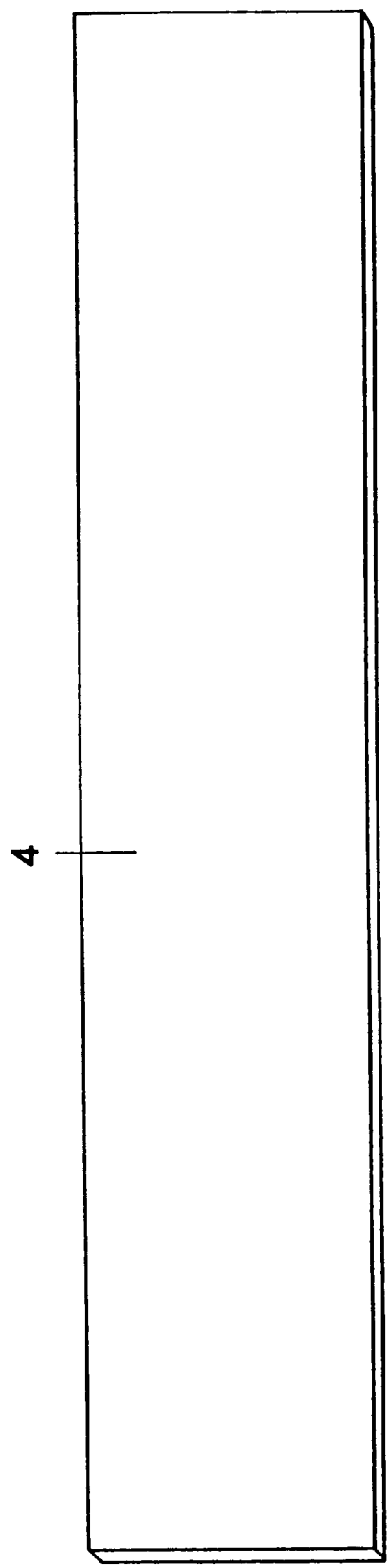

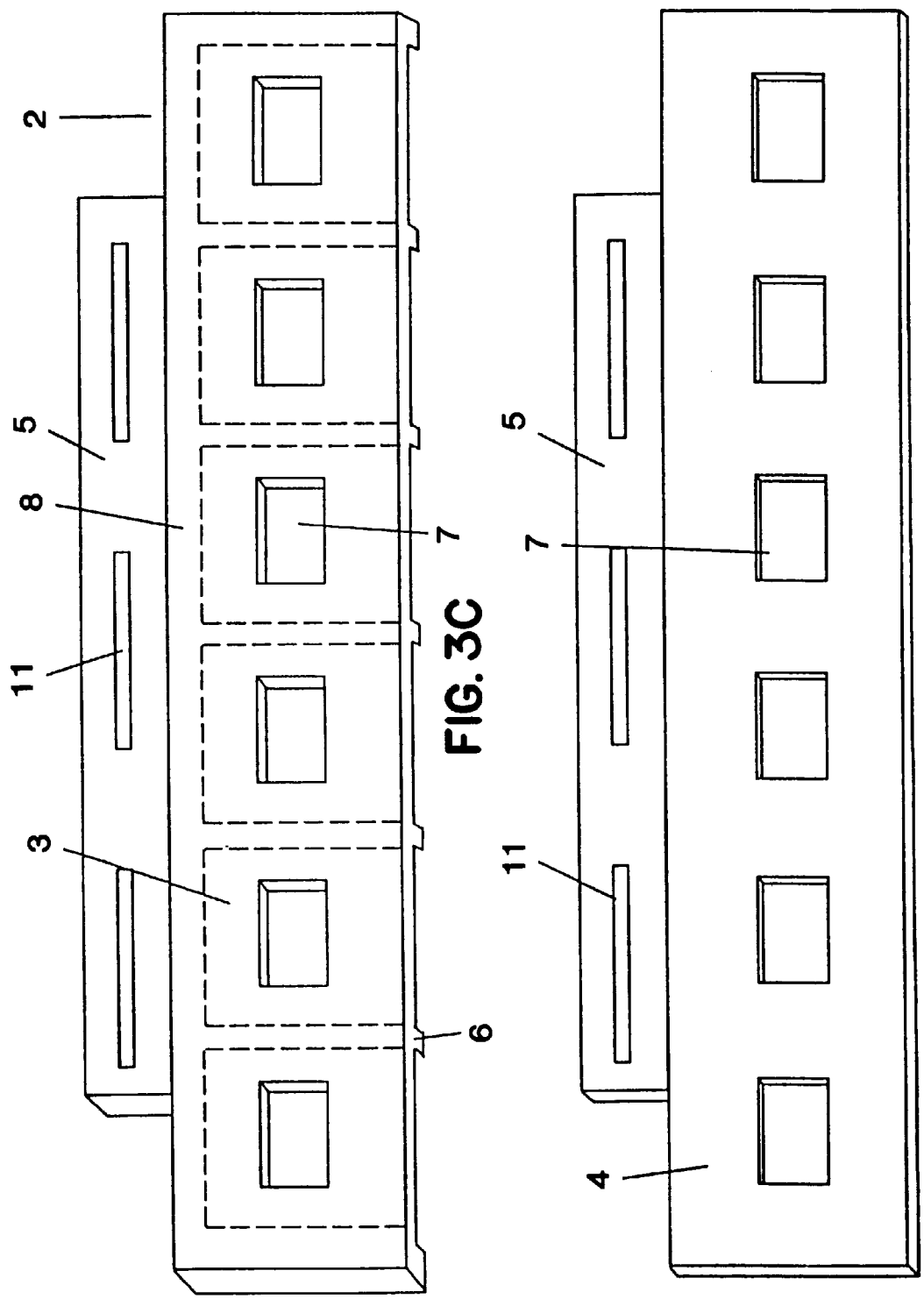

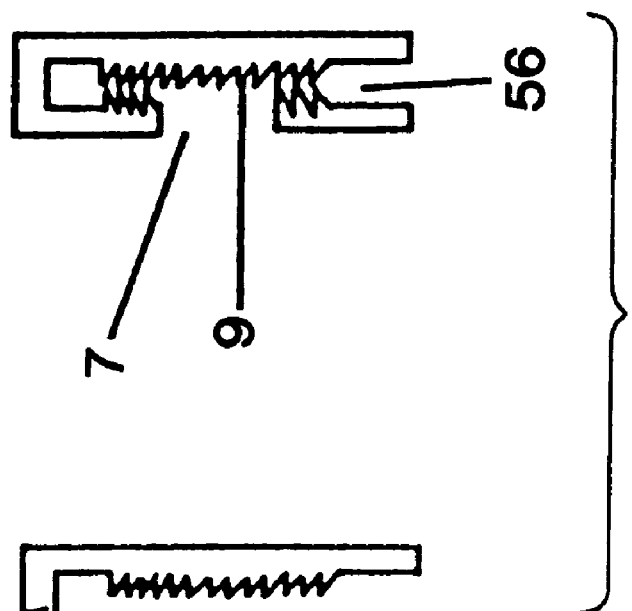
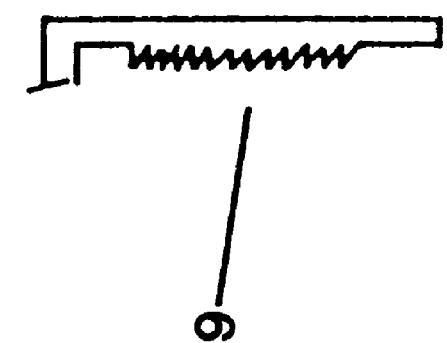
FIG. 3F
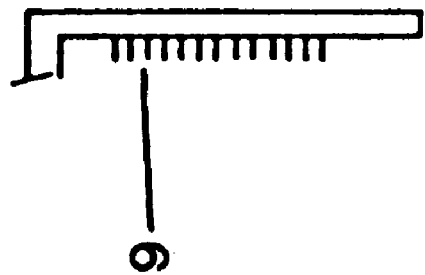
FIG. 3E

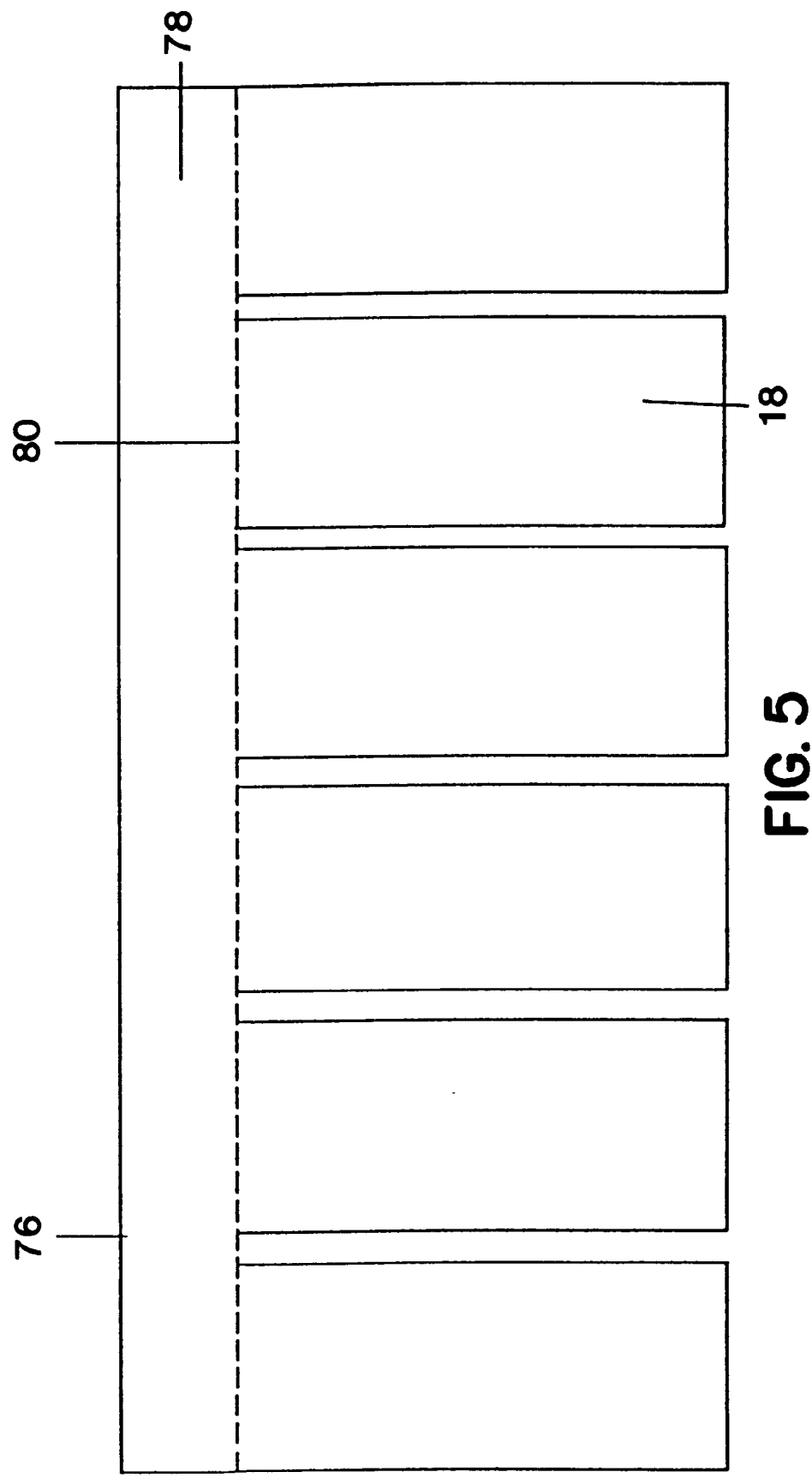

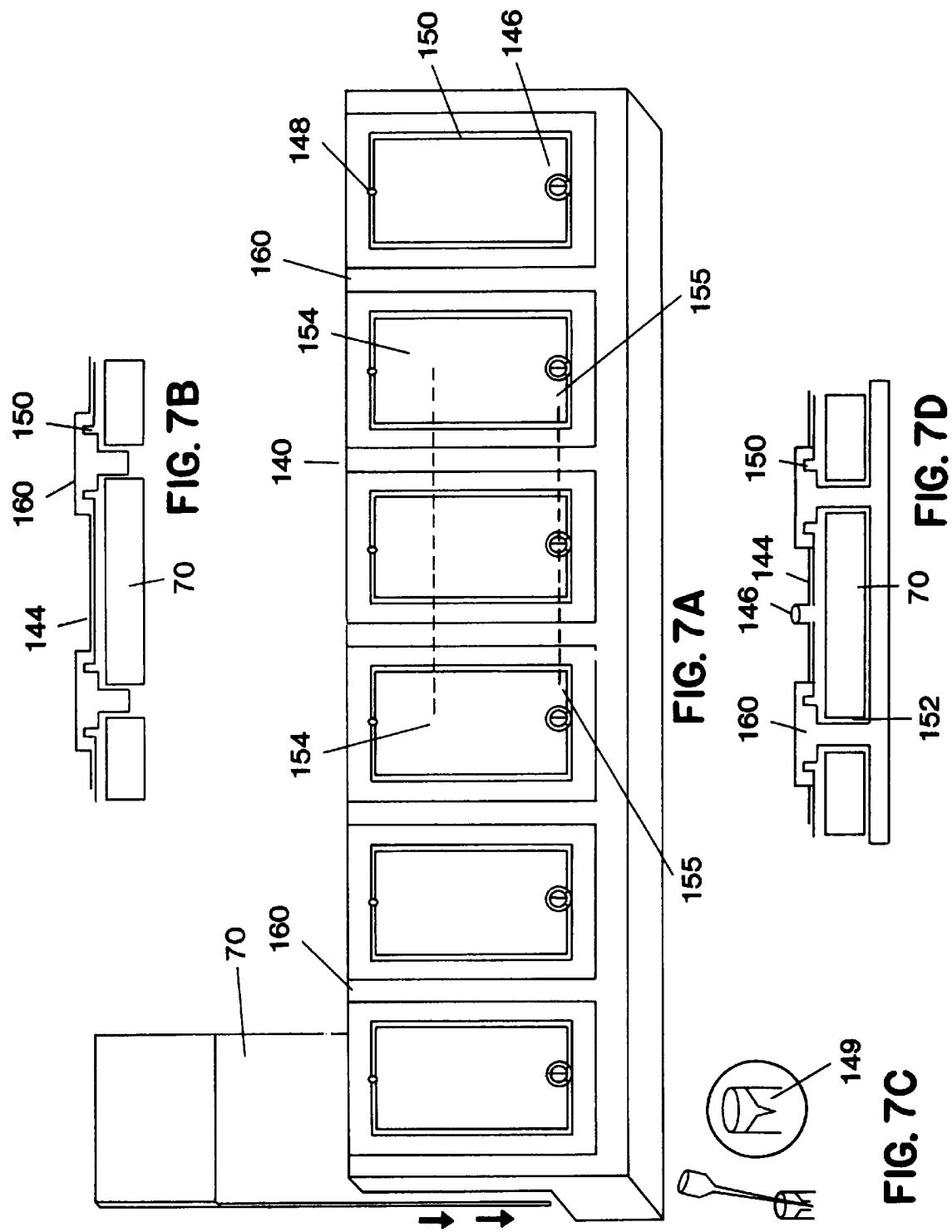

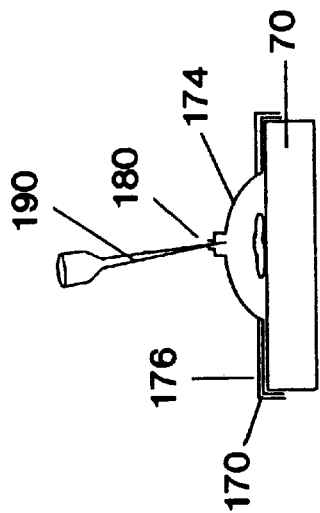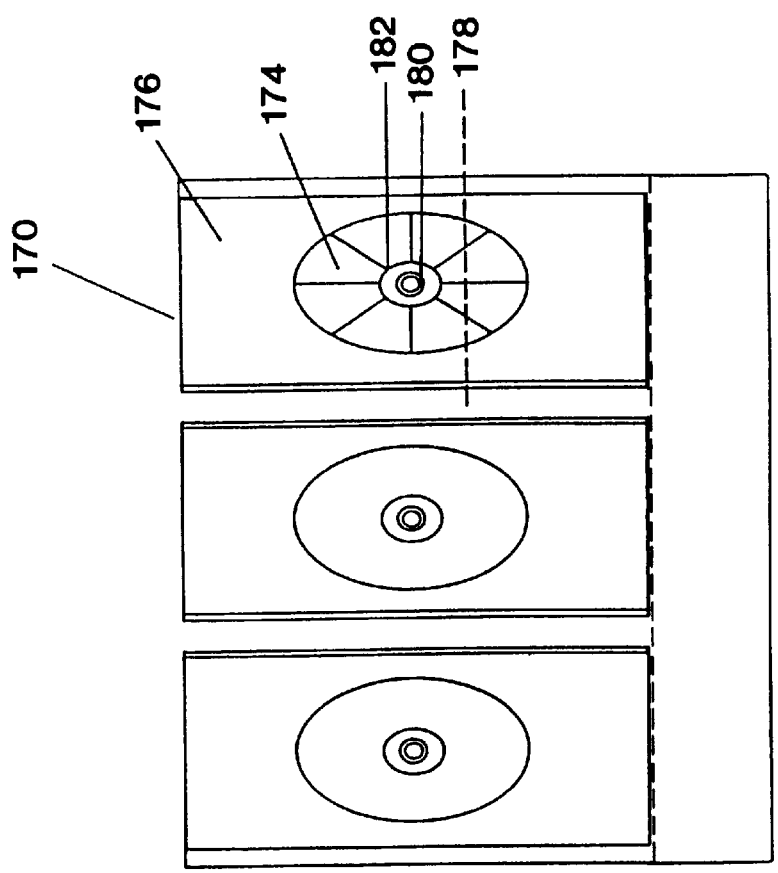

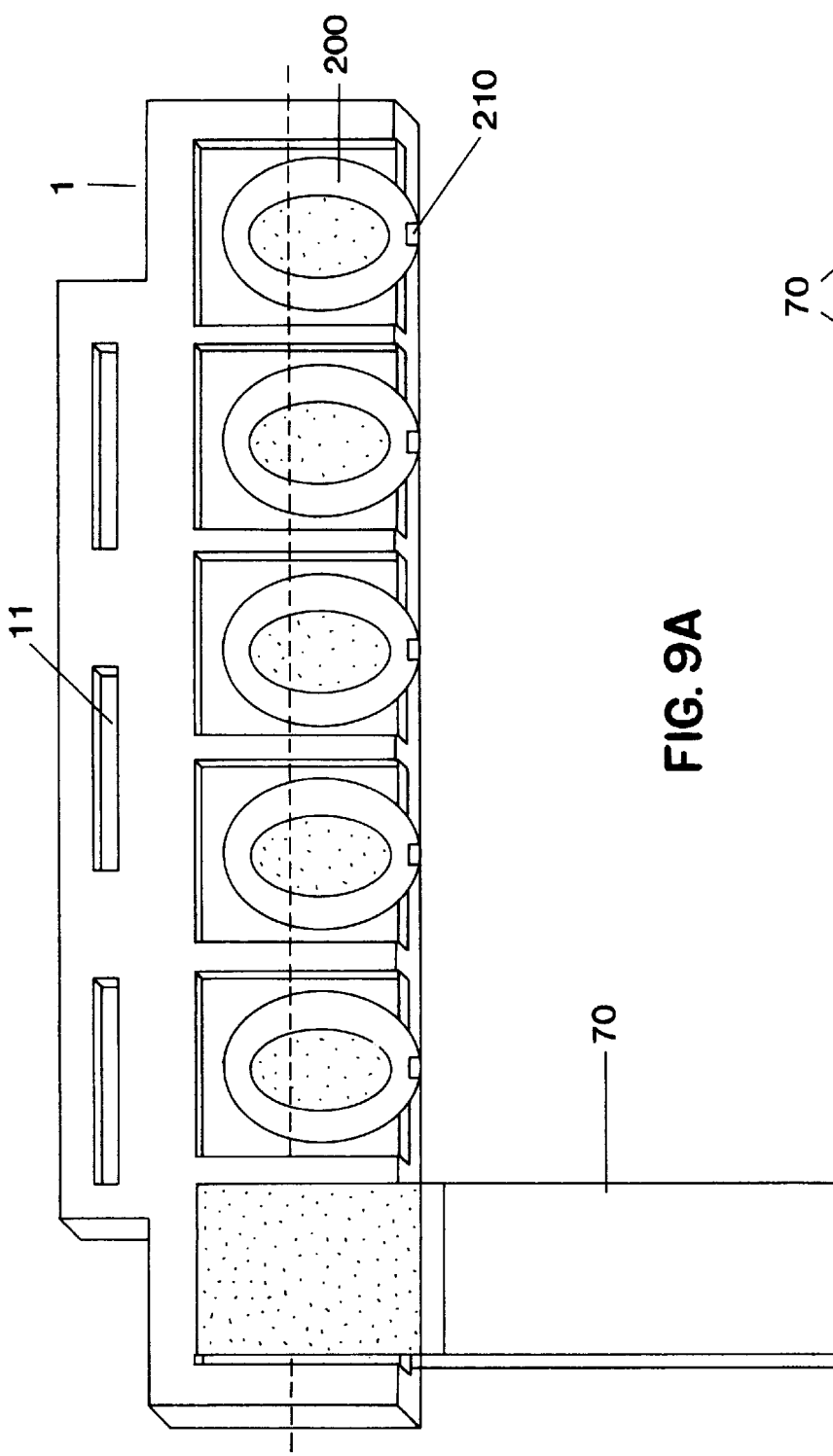
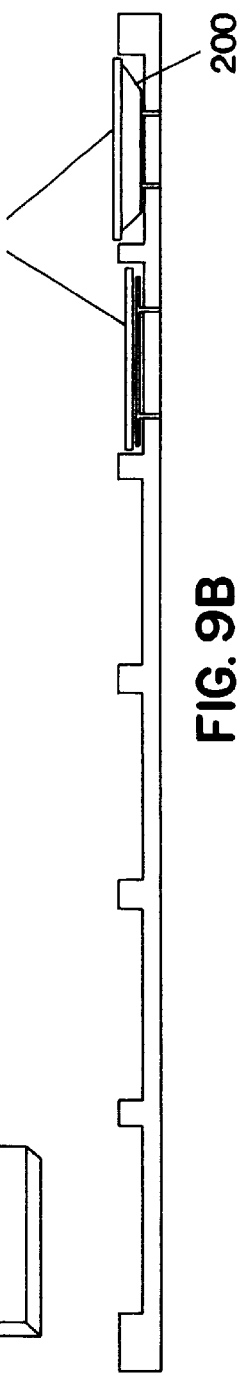
FIG. 9A
FIG. 9B

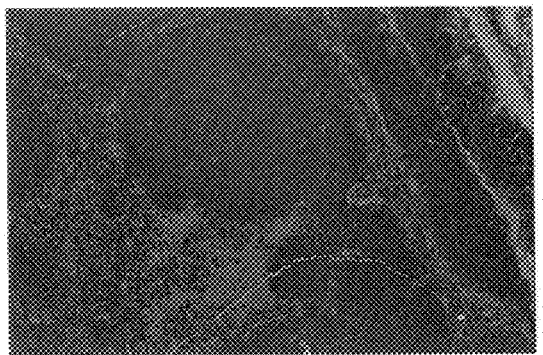
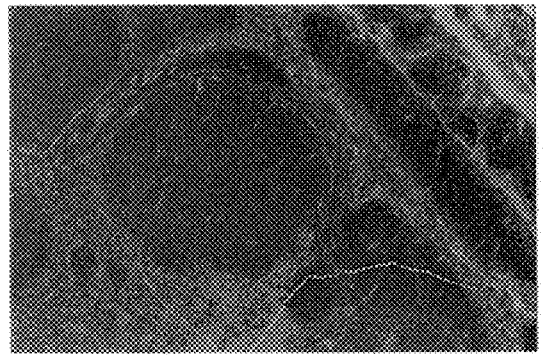
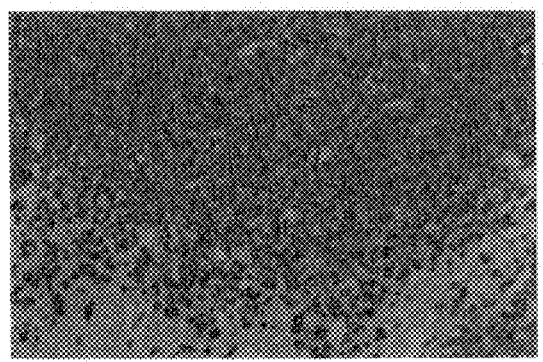
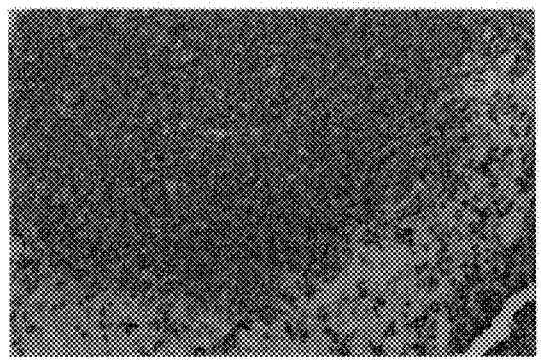

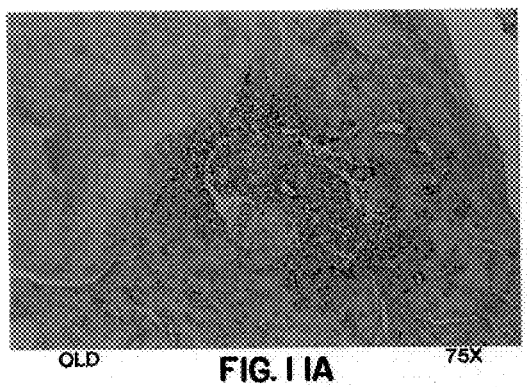 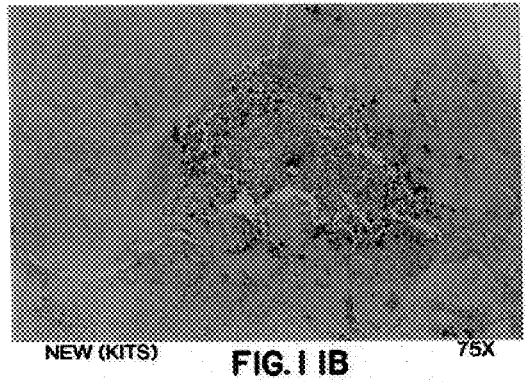
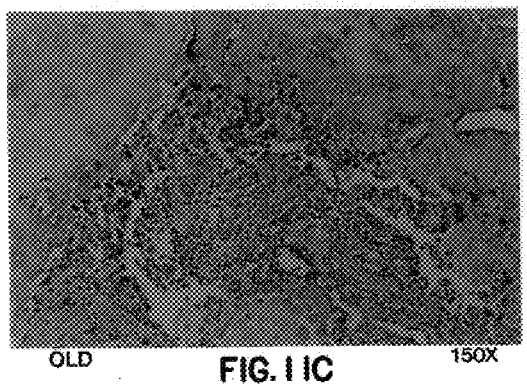 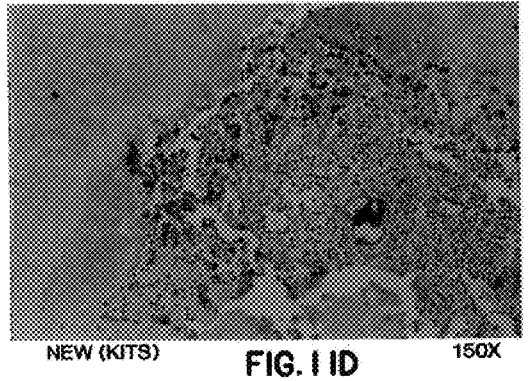
FIG. 11A  FIG. 11B
FIG. 11C  FIG. 11D

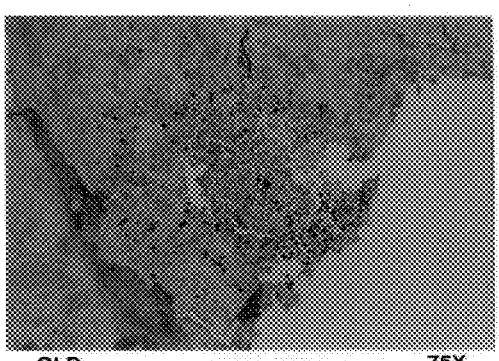
OLD  FIG. 12A  75X
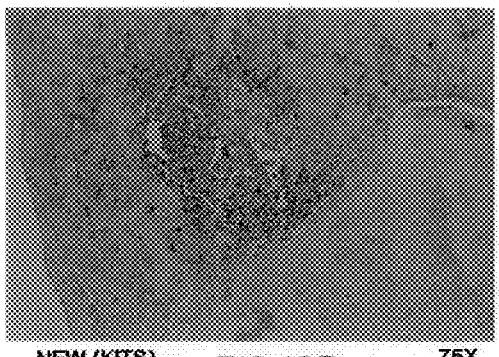
NEW (KITS)  FIG. 12B  75X
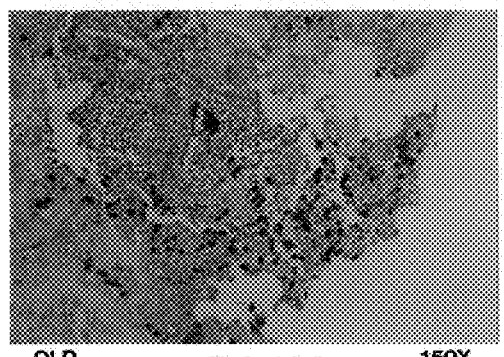
OLD  FIG. 12C  150X
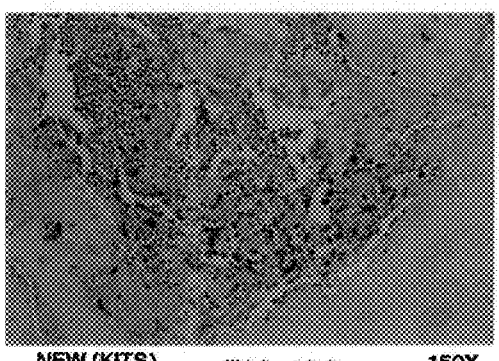
NEW (KITS)  FIG. 12D  150X

APPARATUS FOR EFFICIENT PROCESSING OF TISSUE SAMPLES ON SLIDES

BACKGROUND OF THE INVENTION

This invention relates to an apparatus for processing tissue samples on slides for a wide variety of purposes. Tissue samples are analyzed for many purposes using a variety of different assays. Pathologists often use histochemistry or immunocytochemistry for analyzing tissue samples, molecular biologists may perform in situ hybridization or in situ polymerase chain reactions on tissue samples, etc. Often the sample to be analyzed will be embedded in paraffin and mounted on a microscope slide.

The assays usually involve the use of antibodies, enzymes and other expensive reagents and it is desirable to keep reagent volume use to a minimum to lower costs. These assays are also quite labor intensive although there are now some automated systems (e.g., the Ventana ESIHC Staining System, the Shandon Lipshaw Cadenza Automated Immunostainer; also see D. J. Brigati et al. *Journal of Histotechnology* 11:165–183 (1988)). Most automated systems can only perform 40 to 48 slides per run. Fisher automated systems can perform 120 slides per run. Most automated systems which only perform immunocytochemistry do not perform deparaffinizing, histochemistry (such as hematoxylin and eosin staining) and coverslipping steps and these consequently must be done separately by hand which is time and labor intensive. Furthermore, most commercial ready-to-use reagents are not suitable for automated systems which are required to use specially designed reagents. Laboratories which process very large numbers of samples are likely to be willing to pay the large cost associated with buying these automated systems, but small to intermediate sized laboratories find it more cost effective to continue to process samples manually.

A typical immunocytochemistry assay requires a series of many steps. These include: obtaining a tissue sample such as from a biopsy, fixing the tissue in formalin, processing the tissue overnight, embedding the tissue in paraffin, cutting serial sections and mounting on microscope slides and drying. These steps are followed by steps to deparaffinize (treatments in xylene, ethanol and water), and finally the reaction can be performed on the tissue which has been mounted on the slide. Typically a series of solutions including reagents such as antibodies, enzymes, stains, etc. is dropped onto the slide, incubated, and washed off. Finally the sample may be viewed under the microscope.

Clearly there are many individual steps involved and each sample on a slide must be processed individually. Besides being very labor intensive, there are drawbacks associated with the commonly used method of simply dropping solutions on top of the mounted sample on the microscope slide. The solution is not restricted simply to the area of the tissue sample itself and the solution may be relatively deep rather than being a thin film. These features require use of extra reagents which are quite expensive. Leaving the solutions open to the air as they sit on the slide also may lead to evaporation if the samples must incubate for a long period of time. Evaporation leads to concentration or drying out of the reagents and high concentrations may lead to increased background levels which are clearly undesirable. If the solutions evaporate totally the assay will fail. Incubating samples in humidity chambers with covers may prevent evaporation problems, but water droplets which condense onto the humidity chamber cover may fall onto the slides and this will ruin the assay.

Improved methods for more rapidly assaying several samples at once, but without the high cost of automated systems, will be welcomed by small to intermediate sized laboratories. Furthermore, methods which will allow use of smaller amounts of reagents and overcome the drawbacks of processing samples on slides open to the atmosphere will be a welcome advance.

SUMMARY OF THE INVENTION

The present invention is an apparatus for performing manual assays on tissue samples mounted on microscope slides. One aspect of the invention is a multislide slideholder capable of holding up to six standard microscope slides thereby allowing for the processing of up to six samples at one time. A second aspect of the invention is a multiwell tray containing up to six shallow wells into which reagents are placed and upon which the slideholder plus slides is placed. A third aspect of the invention is a set of prealigned and prespaced coverslips for rapidly placing said coverslips onto the processed slides.

The slideholder is designed in conjunction with the tray. The purpose of the slideholder is to have up to six slides all attached to a single holder so that all the attached slides may be processed simultaneously throughout all of the steps of the staining procedure from deparaffinizing to coverslipping without ever separating the slides from the slideholder. This is a labor intensive step and the ability to process up to six slides at once rather than processing slides individually is an important aspect of the invention. Since one technician typically is capable of easily processing about 40–50 individual slides without mistakes, using a slideholder with six slides per slideholder will allow a single technician easily to perform approximately 240–300 slides for routine histochemistry and immunochemistry staining. This is about 2–6 times as many slides as handled by automated systems per each run.

One useful aspect of the present invention is that any kind of commercial ready-to-use reagents are compatible with the slideholder and there is no need to use specially designed reagents. Another useful aspect is that the apparatus allows a technician to perform different staining procedures on the different slides, e.g., histochemistry and immunocytochemistry or in situ hybridization and in situ PCR at the same time. Other important aspects of the present invention are that it allows one to observe chromogen color development as it is happening and it also gives results which have at least as low a background and sometimes a lower background level of staining than is seen in conventional techniques.

Clearly slideholders capable of holding more than six slides may be envisioned. However there are two practical reasons for utilizing holders capable of holding three or six slides. The first such reason is that the staining dishes in which slides are processed, e.g., washing of the slides, which are presently in use in the typical pathology lab are wide enough to handle only up to six slides side by side at a single time. Therefore a design to hold up to six slides will be compatible with presently used equipment. A second reason for designing a system for processing three or six slides at one time is that in a typical pathology assay three samples must be run together, these being the actual sample being assayed plus a known positive control plus a known negative control. Since a single assay typically requires the use of three slides a system capable of handling six slides allows for the processing of two patient samples at a time.

The slideholder may be designed in different ways. The purpose of the slideholder is to hold up to six microscope slides at one time so that one can easily manipulate the six slides simultaneously with one hand. In one embodiment a reusable slideholder is used. The reusable slideholder is designed to allow the tops of microscope slides to fit into the holder simply by inserting the slides into slots in the holder. The slides will fit firmly so as not to fall out during handling. The holder positions the slides in the slots so that the slides are prealigned to fit onto the wells of the tray containing the reagents which will react with the tissue samples. The thickness of the holder is designed so that it fits into a trough in the tray and keeps the microscope slides level on top of the wells. If the holder is too thick or too thin the slides may not rest properly on top of the wells in the lower tray and proper contact will not be made with the reagents in the wells.

The slideholder need not be a reusable one. In this second embodiment of the invention one end portion of each microscope slide is glued to a slideholder using a glue which is xylene and ethyl alcohol resistant. The glue holds the slides firmly to the slideholder during processing and when the processing, e.g., staining, is completed the slides can be easily separated from the slideholder.

A third embodiment of the invention is a slideholder with suction cups attached wherein said suction cups hold the slides firmly on the slideholder.

A fourth embodiment of a slideholder is one in which the slide holder consists of two plastic portions with ridges wherein one portion is placed onto each side of the slides and then clipped together such that the slides are held between the two portions of the slideholder. The ridges properly align and space the slides. In one variation of this and other embodiments, the slideholder has ribbed surfaces of plastic or rubber which help to hold the slides firmly in place.

In any embodiment of a slideholder it is useful to have a handle portion to make the handling of the slideholder simpler, but the presence of a handle is not essential. If a handle is present it is useful to have holes in the handle through which a "fork" can be inserted such that several (15–20) slideholders can be placed onto a single fork and manipulated together easily. Another useful variation that is applicable to any embodiment of slideholder is to have an opening or a transparent region of the slideholder which acts as a window through which one can see a label attached to the end of the slide which is inserted into the slideholder. Yet another desirable feature which may be used is to have slideholders of various colors which make it simple to determine which slides are undergoing which assay when a variety of assays is being performed.

The tray to contain the reagents such as antibodies and enzymes is an integral part of some embodiments of the invention. The tray is preferably designed with three or six wells although trays with a different number of wells may also be used. In one embodiment of the present invention, each well is shallow to hold a minimal amount of reagent to keep costs low but is deep enough to allow for fluid motion within the well. This overcomes some problems present with systems requiring capillary action of fluid between two slides, especially when viscous reagents must be used. See, Babbitt et al., U.S. Pat. No. 5,002,736; D. J. Brigati, U.S. Pat. No. 4,777,020; Bowman et al., U.S. Pat. No. 4,985,206; and McGrath et al., U.S. Pat. No. 5,192,503. Each well is completely separated from neighboring wells by a trough so that any overflow from one well cannot contaminate a neighboring well. A tray may be designed without these intervening troughs if one is not concerned about contamination between wells, e.g., if all of the wells contain the same solution. The microscope slides with mounted tissue samples are placed tissue side down on top of the wells of the tray and completely cover the wells effectively sealing the wells from the atmosphere. This aspect of the invention prevents evaporation of the small amount of fluid in the well. It further prevents contamination of the reagents in the well and also overcomes the problem of extraneous matter falling on top of the sample such as sometimes occurs when samples are incubated in a covered humidity chamber and drops of water fall onto the surface of the slides. In the present invention any such drops of water fall onto the backs of the incubating slides since the slides are placed sample side down onto the trays.

Another embodiment of the tray is one in which the bottom of each well is made of a soft or pliable material. One advantage to having a soft bottom is that it becomes easy to remove air bubbles which may be trapped between the slide and soft bottom. By pushing on the soft bottom of a well, one can easily remove air bubbles to a region away from the region of the tissue sample. A second advantage to having a soft bottom is that the volume of reagent solution needed in a well becomes flexible.

Another feature of the tray is two notches or channels in the well boundaries and tubing attached to the outside of the boundary at one of these channels. These features allow the slide holder plus slides to be placed onto the tray prior to adding reagents to the tray. The reagent solutions may be added through the tubing. The solutions pass from the tubing trough a first channel while air in the well escapes through a second channel at the top of the boundary.

Other alternate embodiments of the tray may be used but will not necessarily have all of the advantages outlined above. One such alternate embodiment is to design a tray with larger wells such that each well can accommodate multiple slides at one time, preferably 3 or 6. In this design slides are placed into a holder which holds the slides in tight conjunction side by side. In a design with a tray containing wells large enough to require 3 slides to completely cover each well, a slideholder will hold 3 slides in tight conjunction (or 2 sets of 3 slides with a space between the 2 sets). With this configuration it is necessary to make only a single pipetting to fill a well for 3 slides rather than requiring 3 individual pipetting steps for the 3 slides. This is a labor saving advantage. The disadvantage is that the volume of a single well to be covered by 3 slides is greater than 3 times the volume of a well designed to be covered by an individual slide. This is because wells designed for single slides are narrower than the full width of a slide. This alternate embodiment is therefore a tradeoff of requiring fewer pipettings thus saving time vs. the added expense of using slightly more reagent. Furthermore, these larger wells may only be used when each slide is to be treated with the identical reagent. These larger wells are also useful in the cases for which large tissue sections are examined with the single tissue section requiring several slides side-by-side for mounting. Trays with individual wells are suited to treating each slide with different reagents since each well is completely separate from nearby wells.

Another desirable feature which may be used with any embodiment of tray is to have trays of various colors which make it simple to determine which slides are undergoing which assay when a variety of assays is being performed.

A different embodiment of the invention is that rather than a tray, a special multichamber coverslip is placed on top of a slide which has a tissue sample mounted on top of it. This special coverslip consists of three or six conjoined incubation chambers. A further feature of this special coverslip is that the top of each incubation chamber comprises a soft and pliable top rather than simply being a hard coverslip. The purpose of the soft top is to be able to push any trapped air bubbles to a region away from the tissue sample. Another feature is that the special coverslip can include a raised region toward the edges of each chamber which can trap air which is pushed into the region and thus trap air bubbles which have been pushed to the edges thereby preventing the air bubbles from returning to the area of the slide on which the tissue sample is mounted. Another advantage of the soft top is that the volume of reagent solution needed in a chamber becomes flexible.

An alternative embodiment of the special coverslip is to modify it to have tubing on one side of the chamber and a very small hole on the opposite side of the chamber. The tubing may contain a valve through which reagents can be added and by which means the tubing can be closed. The small hole allows air to come out when reagent is added to the chamber. This modification allows the coverslip to be placed onto the slides prior to adding reagent, with reagent later being added via the tubing.

Another desirable feature which may be used with any embodiment of coverslip is to have coverslips of various colors which make it simple to determine which slides are undergoing which assay when a variety of assays is being performed.

The third aspect of the invention is a set of slide covers which are premade as a set of up to six covers connected together and which may be laid on top of the processed slides which are still attached to the slideholder. The dimensions are such that all covers will perfectly line up on the set of slides. The covers are then easily detached from the holder. This may be accomplished by simply breaking them off by having a pre-scored region which allows for easily snapping off the coverslip from a "holder" region to which the slides are attached. The ability to simultaneously align and mount up to six slide covers is a time saving technique which is useful in such a labor intensive process.

BRIEF DESCRIPTION OF THE DRAWINGS

FIG. 1A is a front elevational view of a slideholder 1 showing the front planar surface 10 and the groove 20 which is 1 cm wide, runs the complete length from edge 30 to edge 32 and is 0.4 cm from edge 34 and 2.6 cm from edge 36.

FIG. 1B is a rear elevational view of a slideholder 1 showing the opposing planar surface 12 and two sets of six grooves 40 and 42. Regions 50 bound a side of each slide 70 and form the edges of each slot. Region 60 is a 0.6 cm wide strip extending from edge 30 to edge 32.

FIG. 1E is similar to FIG. 1D but indicates the presence of slides 70 inserted into slots 56.

FIG. 1F is similar to FIG. 1D but shows a simpler slideholder 1 which does not include openings 7.

FIG. 1G is a cross-sectional view of the slideholder shown in FIG. 1D. This shows a slide 70 partially inserted into slot 56. Opening 7 is indicated. This indicates an embodiment of a slideholder which has ribbed surfaces 9 within slot 56.

FIG. 2A is an elevational view of one surface of a slideholder 1. Slides 70 are attached to the slideholder 1 by gluing an end of slide 70 into an indentation 22 between ridges 6.

FIG. 2B shows an edge view of the slideholder 1 shown in FIG. 2A.

FIG. 3A is a front elevational view of one surface 3 of one portion of a third embodiment of a slideholder 1. There are seven raised ridges 6 which align and space the slides 70 parallel to each other and a ridge 8 against which one end of the inserted slide is pushed.

FIG. 3B is a rear elevational view of the third embodiment of a slideholder 1 as shown in FIG. 3A. This opposing surface 4 is a flat planar surface.

FIG. 3C is similar to FIG. 3A except it shows a slideholder 1 with a window 7 through which one can read a label attached to a slide 70. The Figure also illustrates a handle 5.

FIG. 3D is similar to FIG. 3B except it shows a slideholder 1 with a window 7 through which one can read a label attached to a slide 70. The Figure also illustrates a handle 5.

FIG. 3E is a cross sectional view of slideholder 1 taken along line 74—74 of FIG. 3A. This shows a slideholder 1 which has ribbed surfaces 9. These are not shown in FIG. 3A which is a design not including the ribbed surfaces 9.

FIG. 3F is a cross sectional view of slideholder 1 taken along line 74—74 of FIG. 3A. This shows a slideholder 1 which has ribbed surfaces 9 wherein the ribbed surfaces are of a sawtooth pattern. These are not shown in FIG. 3A which is a design not including the ribbed surfaces 9.

FIG. 5 shows coverslips 18 and indicates scoring at scoreline 80.

FIG. 7A illustrates a top elevational view of special multiple chamber coverslip 140. The shaded regions 160 are ridges which extend down between slides and on the edges of the outermost slides 70. Region 150 is a raised region of the coverslip 140 into which air may be pushed and trapped. A small hole 148 through which air may escape is indicated. A tubular opening 146 through which solution may be pipetted is indicated. This opening 146 may contain a valve 149 which seals the opening.

FIG. 7B is a cross sectional view of special multiple chamber coverslip 140 as viewed along line 154—154 in FIG. 7A. This illustrates the raised ridges 150 which create a space into which air may be pushed and trapped. Also seen are the ridges 160 which fit between and around slides 70 and align the coverslip 140. Region 144 which lies in a rectangle inside of raised ridges 150 is made of a soft material.

FIG. 7C is an enlarged view of tubular opening 146 and valve 149 which were shown in FIG. 7A.

FIG. 7D is a cross sectional view of special multiple chamber coverslip 140 as viewed along line 155—155 in FIG. 7A. This shows a slide 70 held between ridges 160, and raised ridges 150 within ridges 160. Slot 152 is the region between ridges 160. This is more clearly seen in FIG. 7E. Tubular opening 146 is also indicated.

FIG. 8A shows a top elevational view of an incubation coverslip 170 suitable for performing in situ PCR. This coverslip 170 consists of a stiff region 176 surrounding a softer region 174. The example shown is one wherein three coverslips are joined together to simultaneously process three samples, these being a positive control, a negative control, and the experimental sample. A framework 182 support the soft top 174. A heat sealable tubular opening 180 for adding solution may be included.

FIG. 8B shows a cross sectional view along line 178 of FIG. 8A. This shows the coverslip 170 sitting on a slide 70 and illustrates the soft top region 174 surrounded by the stiffer region 176. Also shown are a tube 180 in the soft top region 174 and a pipet tip 190.

FIG. 9A shows a slideholder 1 which uses suction cups 200 to hold slides 70 to the slideholder 1. The suction cup 200 is shown with an optional tab 210 which is lifted to break the vacuum between the suction cup 200 and the slide 70. Although circular suction cups 200 are illustrated, other shapes are within the scope of the invention.

FIG. 9B shows an edge view of the slideholder 1 shown in FIG. 9A. The rightmost slot shows a suction cup 200 prior to being depressed by slide 70. The slot to the left of this shows the suction cup 200 depressed by slide 70 which is thereby affixed to the slideholder 1.

FIGS. 10A–D show normal lymph nodes that were formalin-fixed overnight at room temperature and immunohistochemically stained with CD20 (L26) monoclonal antibody at a 1:250 dilution. FIGS. 10A and 10C show results when CD20 antibody was dropped onto the slides for staining via the commonly used procedure. These show a magnification of 30× and 150× respectively. FIGS. 10B and 10D show the results when the staining was performed using the present invention. These show a magnification of 30× and 150× respectively. Here the CD20 was dropped into the wells of the tray. Note the increased intensity of immunostain with decreased background staining in the sample which was processed using the present invention.

FIGS. 11A–D show a normal lymph node that was formalin-fixed overnight at room temperature and immunohistochemically stained for immunoglobulin kappa light chains polyclonal antibody 1:25,000 dilution. FIGS. 11A and 11C show the results using the standard method of dropping antibody directly on the slide. These show a magnification of 75× and 150× respectively. This resulted in a high background staining. FIGS. 11B and 11D show results when the staining was performed using the tray assembly of the present invention and dropping solution into the tray. These show a magnification of 75× and 150× respectively. This resulted in a lower background level of staining with overall stronger staining.

FIGS. 12A–D show, a normal lymph node that was formalin-fixed overnight at room temperature and immunohistochemically stained for immunoglobulin lambda light chains polyclonal antibody 1:50,000 dilution. FIGS. 12A and 12C show the results using the standard method of dropping antibody directly on the slide. These show a magnification of 75× and 150×, respectively, and show the resulting high background staining. FIGS. 12B and 12D show results when the staining was performed using the tray assembly of the present invention and dropping solution into the tray. These show a magnification of 75× and 150× respectively. These show a lower background level of staining with overall stronger staining.

DETAILED DESCRIPTION OF THE INVENTION

Figure 1C:
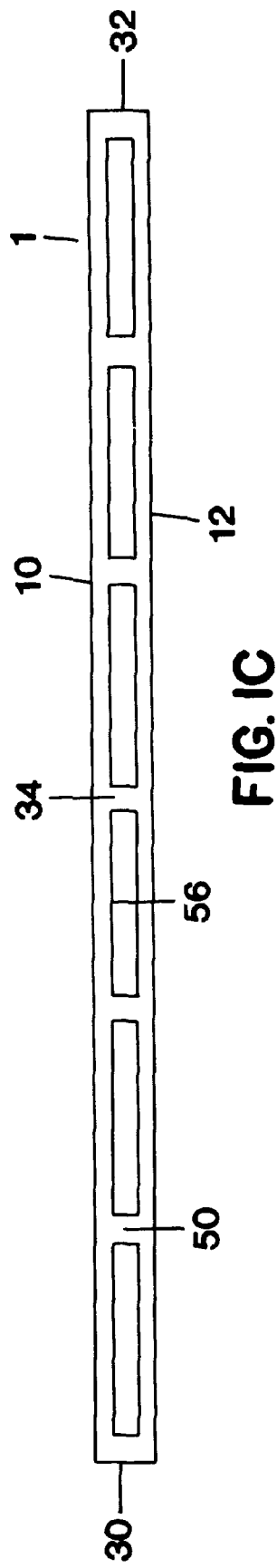
FIG. 1C is a view of a slideholder looking end on at edge 34 showing slots 56. Front planar surface 10, opposing planar surface 12, boundary regions 50, and edges 30 and 32 are also indicated.

The present invention is an integrated system for manually processing tissue samples on microscope slides in a more rapid and efficient and less costly manner than is typical. The system consists of a slideholder 1 and a tray 14 or a coverslip 140 for simultaneously holding up to six microscope slides 70 to allow for concurrent processing of the six slides 70. The slideholder 1 may be reusable. Some embodiments of slideholders are shown in FIGS. 1–3. The holder 1 must not be so thick that it is thicker than the trough 90 in which it sits in the well-containing tray 14. If the holder 1 is too thick the microscope slides 70 will not lie flat on top of the wells 24 and there will be poor contact with the reagents inside of the wells 24. If the holder 1 is thinner than the trough 90 in which it sits there may be a problem in that if the holder 1 is too heavy it will fall to the bottom of the trough 90 and cause the slides 70 to angle up above the wells 24 and result in poor contact with the reagents in the wells 24. If the holder 1 is not so heavy then the weight of the slides 70 will cause them to remain flat on top of the wells 24 and the fact that the holder 1 is thinner than the depth of the trough 90 will be of no consequence. A different solution to this problem is to have a hook 66 which grabs the top of one edge of a slide 70 and holds the slide against the well boundary 44 thereby preventing the slideholder from falling into trough 90. This helps to ensure that the tissue sample on all slides 70 will make good contact with the reagents in the wells 24.

One embodiment of a slideholder is shown with reference to FIGS. 1A–1C. The slideholder 1 may be made of a stiff plastic material such as polyethylene, polypropylene or polycarbonate or any of the other suitable plastics which are xylene and alcohol resistant and which are well-known to those in the art. An example of suitable dimensions for the slideholder 1 is 17.5 cm×4 cm. The slideholder 1 preferably contains 6 slots 56 2.6 cm (slightly larger than the width of a standard slide) by 0.1 cm (the thickness of a standard slide) into which slides 70 are inserted. Each slot 56 is deep enough to allow approximately the top 1.9 cm of each slide 70 to be inserted. Each slot 56 is separated from a neighboring slot 56 by 0.3 cm. This slideholder 1 will hold the slides 70 firmly in place and properly align and space the slides 70 to fit the exemplary tray 14 described above.

The slideholder 1 may be machined from a rectangular planar piece of a rigid plastic material of dimensions 17.5×4×0.3 cm. The front planar surface 10 is machined to carve out a groove 20 1 cm in width and very slightly less than 0.2 cm in depth traversing the full 17.5 cm length of the holder 1. Groove 20 is at a distance 2.6 cm from edge 36 of the holder 1 and 0.4 cm from edge 34 of the holder 1. The back or opposing planar surface 12 of the holder 1 is machined to carve out two sets of six grooves 40 and 42. The first set of 6 grooves consists of grooves 42 2.6 cm long and 0.65 cm wide said width being measured from edge 34 of said holder 1 toward edge 36 of said holder 1. Each groove 42 is made very slightly less than 0.2 cm in depth from the opposing face 12 toward the front face 10. Each groove 42 is separated from any neighboring groove 42 or from a side edge of the holder 1 by an approximately 0.3 cm region 50 of plastic which is not machined thus leaving said regions 50 0.3 cm in depth from the front planar surface 10 to the opposing planar surface 12. A second set of 6 grooves 40 is machined into the opposing planar surface 12 such that there is a distance of 0.6 cm between edge 46 of the set of 6 grooves 40 and edge 40 of the set of 6 grooves 42. The set of grooves 40 exactly aligns with the set of grooves 42 with each groove 40 being 2.6 cm long, 0.65 cm wide and very slightly less than 0.2 cm in depth with unmachined regions 50 of 0.3 cm between each groove 40. The holder 1 which results from inserting groove 20 across the front planar surface 10 and the two sets of grooves 40 and 42 into the opposing planar surface 12 is a holder consisting of 6 slots 56 which are partially enclosed on both surfaces and into which can be inserted approximately 1.9 cm of each of 6 slides 70. The slides 70 are held firmly in each slot 56 by the tension of the plastic surfaces but the slides 70 are easily removable by gently pulling on them.

Figure 1D:
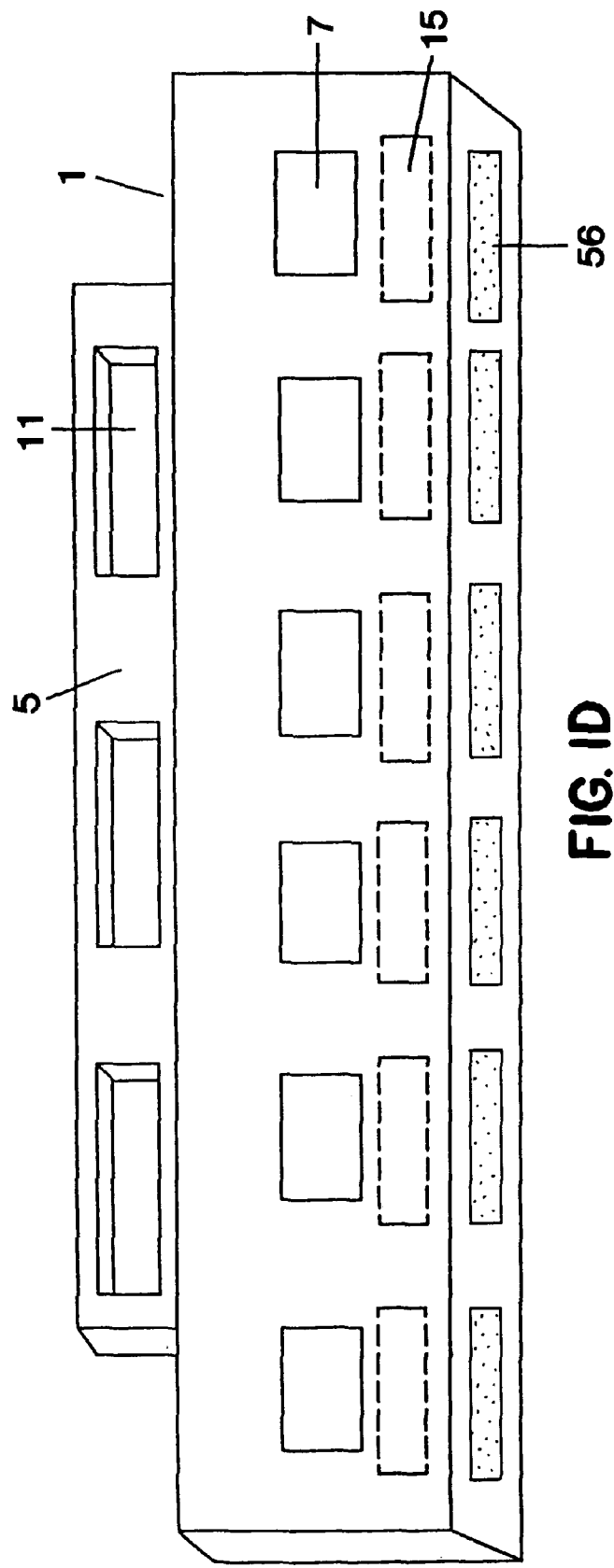
FIG. 1D shows a slideholder 1 with a handle 5. The handle 5 has holes 11 through which a fork 100 (not shown) may be inserted. The slideholder 1 has openings 7 through which may be seen labels which are on the slides 70. Position 15 is a space on the slideholder 1 to which a label may be attached. Slides 70 are inserted into slot 56.

The above description is only one example of a slideholder which may be used for the present invention and is not meant to be limiting. Many differently designed slideholders may be envisioned which may be made with different dimensions or even in quite different manners. The slideholder need not be manufactured in the manner described above but may be made by a molding process, a different machining process, or other methods well-known to those of skill in the art. Slideholders such as shown in FIGS. 1D–1F may be prepared.

A second embodiment of a slideholder 1 is shown in FIG. 2 and is simply a rectangular strip of material, preferably plastic, with indentations 22 on one face to which 6 slides 70 are attached by some means such as a glue which is xylene and alcohol resistant applied to region 22 such that the slides 70 may be easily removed from the rectangular strip. The slides 70 are attached such that there is a 0.3 cm gap between neighboring slides 70. These dimensions will properly align the slides 70 to fit into the tray 14 mentioned above.

FIGS. 3A and 3B illustrate a third embodiment of a slideholder 1. In this embodiment the slideholder 1 comprises two plastic pieces 2 which are held together by a binder clip or by glue. Either one or both pieces 2 of this third embodiment have substantially parallel ridges 6 on one surface 3, said ridges 6 being 2.5 cm apart with each ridge 6 0.3 cm wide. The other surface 4 of this slideholder 1 is a flat surface. The combined height of opposing ridges 6 on the two pieces 2 is less than the depth of a slide 70, this generally being 0.1 cm. These ridges 6 align the slides 70 properly and allow the plastic pieces 2 to firmly hold the slides 70 in place when slides 70 are placed between them and a clip is placed on the plastic pieces 2 to hold them together or alternatively the pieces 2 are glued together. The clip must fit properly into trough 90 of tray 14 to allow the slides 70 to lie flat on wells 24. In a preferred embodiment both pieces 2 of this embodiment of the slideholder 1 are identical. It is not necessary that the two pieces 2 be identical, for example one piece 2 could have ridges 6 and the second piece 2 could be flat with no ridges 6, the ridges 6 on a single piece 2 being enough to properly align the slides 70. A preferred embodiment further has a ridge 8 against which the top edge of each slide 70 is pushed so that an equal length of each slide 70 is protruding from the slideholder 1.

FIGS. 3C and 3D illustrate an alternative design which incorporates an opening 7 in the slideholder 1 through which it is possible to read a label attached to a region of the slide 70 which is inserted into the slideholder 1. This opening 7 may be present in either one or both pieces of the slideholder 1.

Other variations of the above embodiments are possible. The first embodiment described above may be formed by using two pieces of plastic which are later sealed together rather than machining a single piece of plastic to form the slideholder 1. In such a case and in a slideholder 1 such as the third embodiment described above, it is possible to attach ribbed surfaces 9 of plastic or rubber or to machine ribs into the slideholder 1. FIGS. 1G, 3E and 3F illustrate these ribbed surfaces 9. The ribbed surfaces 9 aid in preventing an inserted slide 70 from slipping out of the slideholder 1.

Yet another embodiment of a slideholder 1 is one wherein slides 70 are attached to slideholder 1 by means of suction cups 200 which are mounted on slideholder 1. Such an embodiment is illustrated in FIG. 9. Suction cups 200 may comprise a tab 210 which when pulled releases the vacuum between the suction cup 200 and a slide 70.

Another aspect of the invention is to color code the slideholder and the handle of the slideholder. For each different procedure a different color of slideholder and handle may be used. For example, the handle color may be used to indicate whether the sample is for histochemical staining, immunocytochemistry, in-situ PCR, etc. The slideholder in turn can have its own color which may be different from or the same as the color of the handle. The slideholder may even consist of multiple colors. The slideholder color can be indicative of information, e.g., to indicate whether a sample has or has not been digested, is being treated with a monoclonal or a polyclonal antibody, etc. The color coding scheme is a matter of personal choice.

Figure 4A:
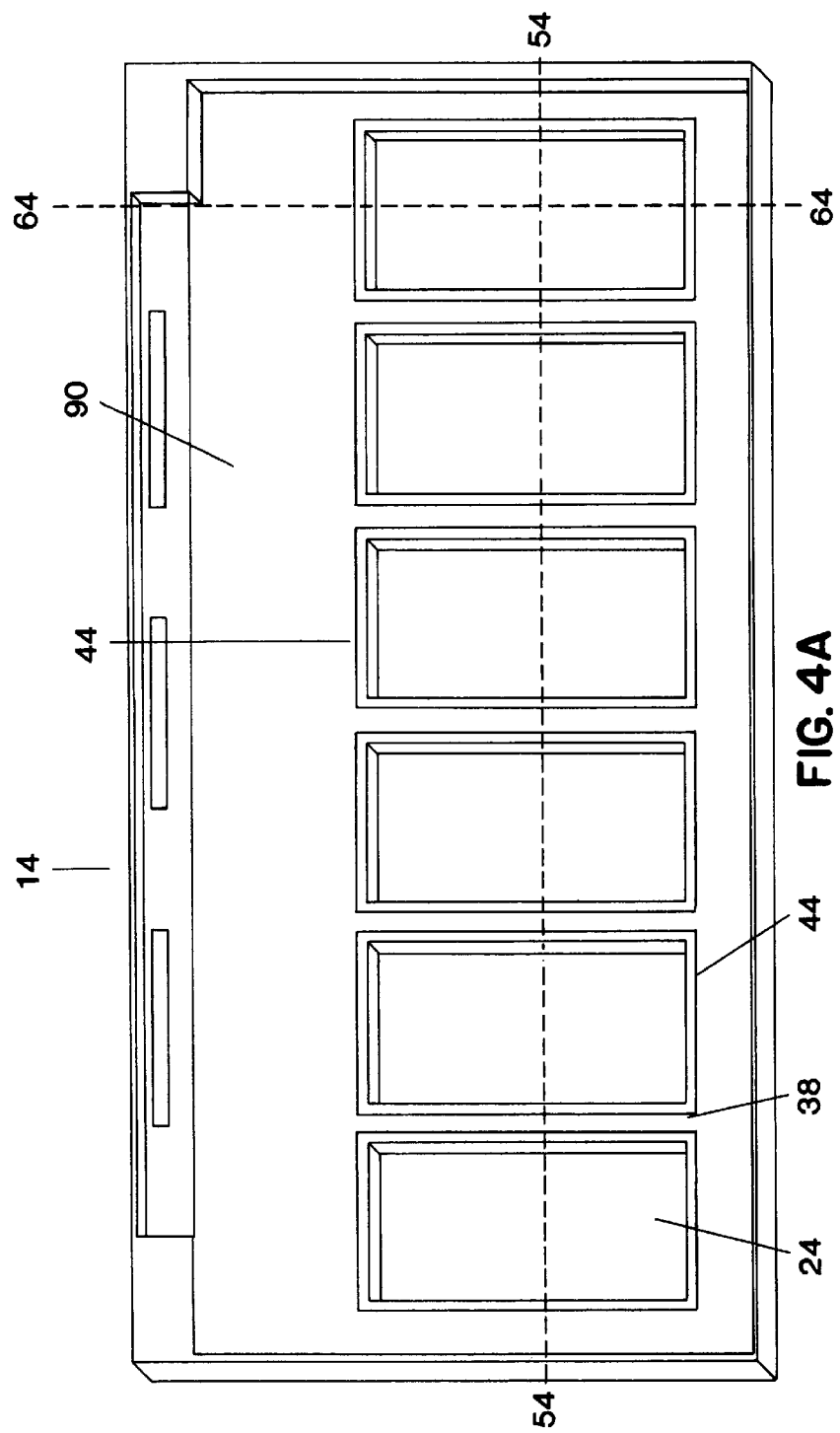
FIG. 4A is a front elevational view of a tray 14. Wells 24 are separated by troughs 38. Boundaries 44 of wells 24 are flat and are elevated above the interior portion of the wells 24.
Figure 4B:
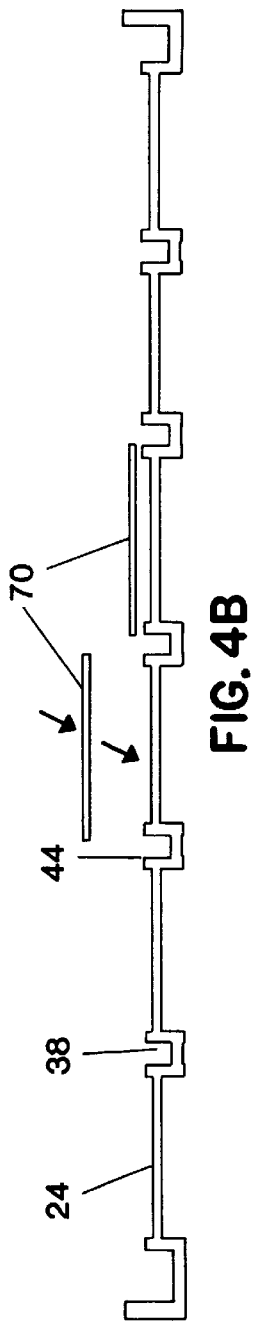
FIG. 4B is a cross sectional view of the tray 14 taken along line 54—54 of FIG. 4A. This view shows wells 24, troughs 38, and well boundaries 44. Slide 70 is shown resting on one well 24.

The slideholder 1 plus slides 70 is placed on top of a multiple well tray 14 which contains up to six individual wells 24 or 1 or 2 large wells 24 with each large well 24 to be covered by 6 or 3 slides 70 respectively. FIG. 4A is a representation of one embodiment of the tray 14. An example of the dimensions of such a tray 14 is (see FIG. 4): outer dimensions of tray 14 19×11 cm; outer dimensions of each well 24 of 2.2×4.7 cm, inner dimensions of each well 24 1.8×4.3 cm (therefore leaving a flat edge 44 0.2 cm wide surrounding each well 24 and upon which each slide 70 will lie); a space or trough 38 between each well 24 of 0.3 cm. Each well 24 is raised above the height of the trough 38 by approximately 0.1 cm with the edges 44 surrounding the well 24 being approximately 0.1–0.3 mm above the center region of the well 24. These values are exemplary only and are not meant to limit the invention. The listed values are appropriate for standard sized slides (25×75 mm), allow for using small amounts or reagents, and space the slides 70 closely enough that 6 slides 70 will fit within the width of a standard staining dish. The type of material from which the tray 14 is made will depend on the type of assay being formed. For many purposes the tray 14 may be made of a thin, moldable plastic material. It may be desirable to use a clear, transparent material so that wells 24 can be viewed from beneath. Such trays 14 are easily manufactured and may be used once and disposed. If the tray 14 is to be subjected to high temperatures such as occurs with polymerase chain reactions, it will be more appropriate to manufacture the tray 14 of aluminum which is capable both of withstanding the high temperatures to which it will be exposed and of efficiently conducting heat which is a necessity for the polymerase chain reaction to work properly.

In a preferred embodiment each well 24 is separated from the neighboring well 24 by a trough 38. This trough 38 prevents cross-contamination between wells 24. The depth of each well 24 is approximately 0.1 to 0.3 mm and will hold approximately 75–200 μL of solution. Trays 14 with wells 24 of different depths may be desirable for specific types of reactions. Deeper wells 24 (on the order of 0.3 mm) may be used when it is desirable to have a larger amount of reagent present and yet prevent the necessity of having the reagent very concentrated. Conversely a tray 14 with shallower wells 24 may be used when a smaller amount of reagent is adequate for the desired purpose. The use of smaller amounts of expensive reagents is one of the advantages of the present invention. As can be seen in FIG. 4A, the tray 14 consists of three or six wells 24 with each well 24 surrounded by a trough 38. The trough 38 is extended to include trough 90 into which the slideholder 1 can fit. This area is necessary for a reusable slideholder 1 to allow the microscope slides 70 to lay flat on top of the wells 24. The thickness of the holder 1 underneath the slides 70 must be no greater than the depth of the trough 90.

Figure 4C:
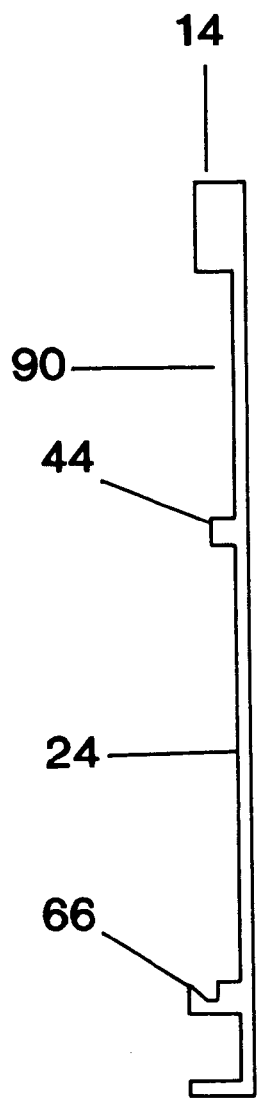
FIG. 4C is a cross sectional view of the tray 14 taken along line 64—64 of FIG. 4A. This shows the hook region 66 which aids in keeping slides 70 pressed against the tray 14.
Figure 4F:
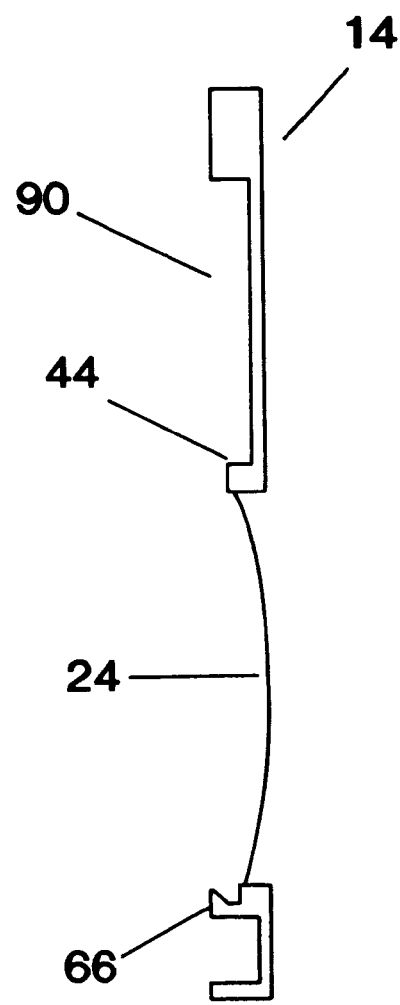
FIG. 4F is a cross sectional view of the tray 14 along line 64—64. This illustrates hook region 66.
Figure 4D:
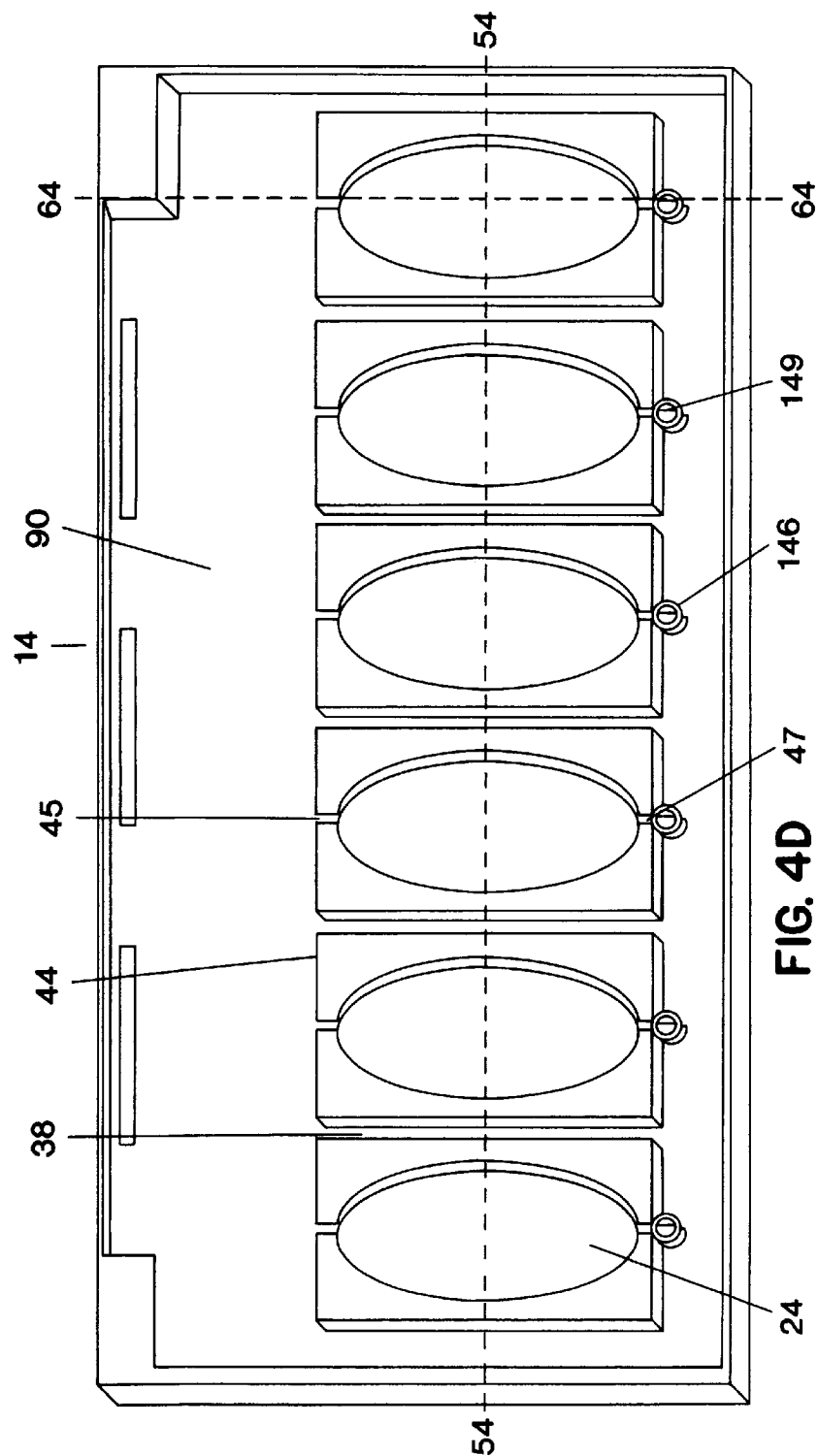
FIG. 4D shows a soft-bottomed tray 14. Wells 24, troughs 38 and well boundaries 44 are indicated. A notch or channel 45, to allow air to escape, in the boundary 44 is shown. Tubing 146 through which to apply solution to the well 24 via channel 47 is shown. Tubing 146 includes a valve 149.
Figure 4E:
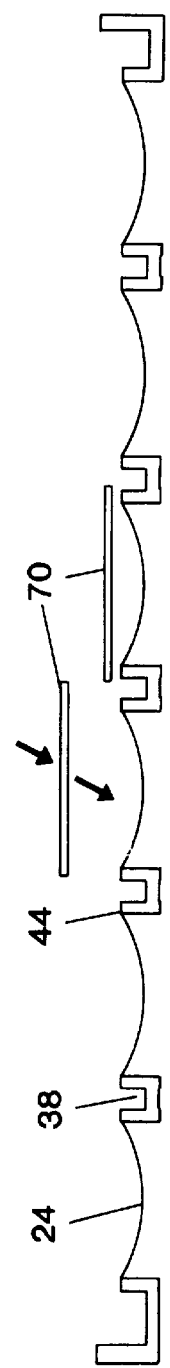
FIG. 4E is a cross sectional view of the tray 14 along line 54—54 taken through all six wells 24 shown in FIG. 4D. A curved bottom of wells 24 indicates that these are soft bottomed wells. Troughs 38 and well boundaries 44 are shown. A slide 70 is shown resting on top of one well 24.

In practice, a tissue sample is mounted onto each of the slides 70 to be analyzed. This often involves steps of fixing a tissue sample in formalin, embedding the sample in paraffin, cutting thin, serial sections from the paraffin, and mounting the sections onto the microscope slides 70. These are dried overnight at room temperature. The mounted tissue sections are subjected to some type of assay such as staining. For this the mounted samples must be placed in contact with a series of solutions with washing steps in between each different change of reagent. In the present invention the reagents are measured into each well 24 in the trays 14. Enough reagent is added to completely fill the well 24 such that the solution in the well 24 will contact the microscope slide 70 which is to be laid on top of the well 24. There should be no air bubbles present between the solution in the well 24 and the microscope slide 70. By exactly filling the well 24 or by slightly overfilling the well 24 so that there is a slight overflow once the slide 70 is placed on top of the well 24 (surface tension holding the top of the solution in the well 24 prior to a slide 70 being placed onto it) there is no problem with air bubbles forming. Capillary action of the fluid in the well 24 contacting the slide 70 allows for good contact between the tissue and reagents across the complete well 24 area and helps to seal the well 24. Trays 14 may be designed to include a hook 66 on one edge of a well boundary 44. This is shown in FIGS. 4C and 4F. By pushing all of the slides 70 against the hooks 66 all of the slides will be held against the well boundaries 44 and this will assure good contact with the reagents within the wells 24.

By placing the slides 70 onto the tray 14 in the above manner, the mounted tissue is facing down into the well 24 and is not exposed to the atmosphere. This prevents extraneous material from falling into the reagent or onto the tissue sample during incubation. Furthermore, the slide 70 covers the well 24 and helps to prevent evaporation of the reagent solution in the well 24 during incubation. Evaporation may lead to very bad background signals. The present invention helps to overcome this problem.

Figure 6:
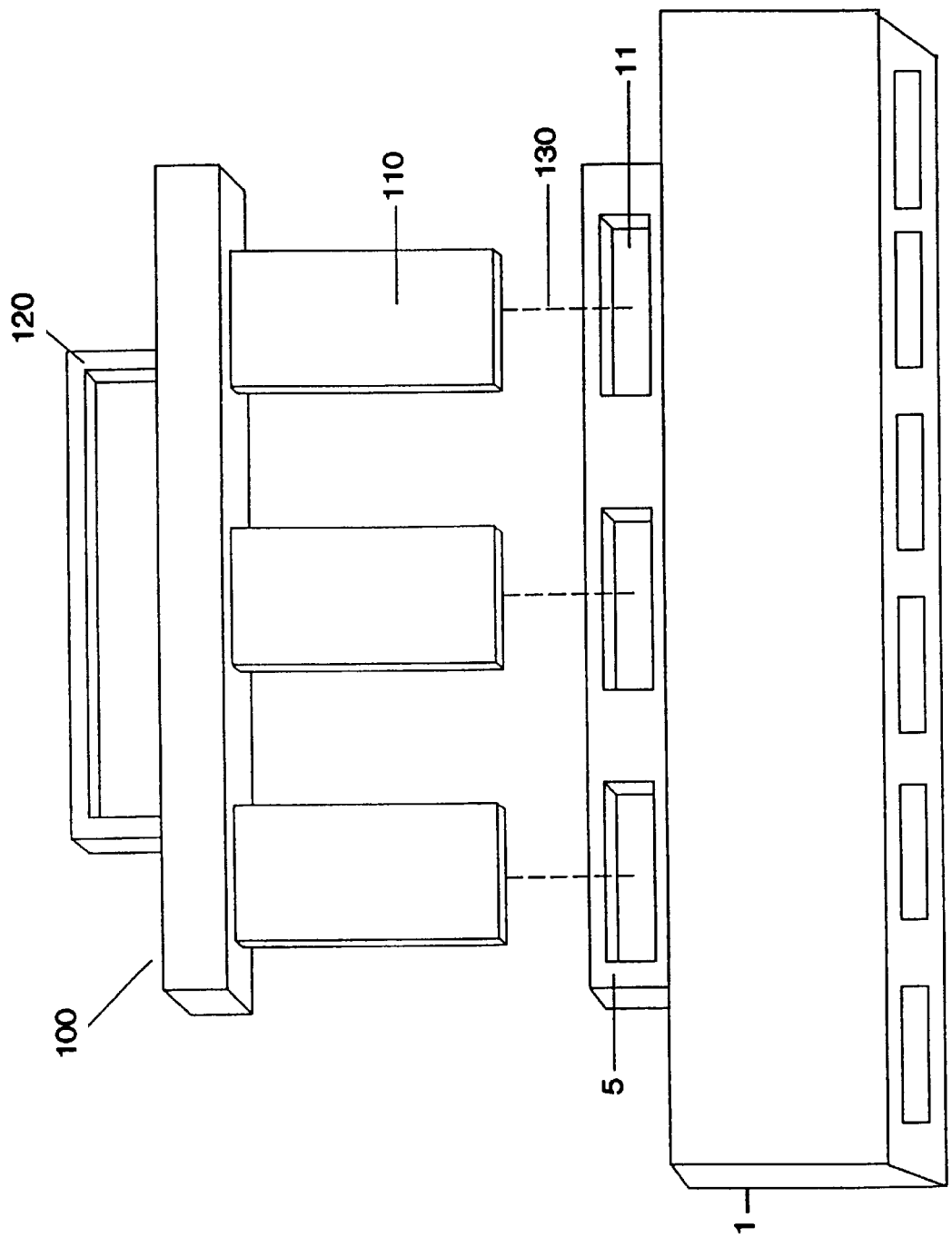
FIG. 6 illustrates a fork 100 and the alignment of tines 110 of fork 100 with holes 11 in the handle 5 of slideholder 1.

After incubation with each reagent the slideholder 1 and tray 14 are picked up and put into a standard staining dish with 500 milliliters of phosphate buffered saline (PBS) solution. Once in the PBS, the surface tension between the slides 70 and the tray 14 disappears and the slides are very easily removed from the tray. The slides are then put through the appropriate washing steps. It is a simple matter to pick up six slides 70 at once since they are all attached to a single holder 1. A standard staining dish in a laboratory is large enough to accommodate six slides 70 across (as attached to a single slideholder 1) and can contain 20 slideholders 1. Therefore 120 slides 70 may be washed and processed simultaneously. If slideholders 1 with handles 5 containing holes 11 in them are utilized, it is very convenient to slide the tines 110 of a single fork 100 through the holes 11 of several slideholders 1, even up to at least 20 slideholders 1, at one time. This is illustrated in FIG. 6. The dashed lines 130 in FIG. 6 indicate how the tines 110 fit through the holes 11 of the slideholder 1. All of the slideholders 1 are then picked up and moved between staining dishes simply by picking up a single fork 100. The fork 100 may have a handle 120 for ease of use. In the third embodiment of slideholder 1 described above which used a clip or glue to hold together two pieces of the slideholder 1, the clip acts as a handle 5 and may be made to have holes 11 through which the tines 110 of fork 100 may be placed. If glue is to be used, the slideholder 1 may be designed with a handle 120 so that no clip is necessary.

Following the processing of a sample it is customary to place a coverslip 18 onto each slide 70. This is customarily done one slide 70 at a time. The present invention makes this chore easier by having premanufactured coverslips 76 which are connected in groups of three or six and which are spaced to properly line up with the three or six slides 70 in the slideholder 1. Up to six coverslips 18 may be picked up at once and aligned over three or six slides 70 simultaneously. The coverslips 18 are usually a thin piece of glass or plastic. These may be manufactured to be prescored so that each individual coverslip 18 easily snaps off from its holder 70. FIG. 5 shows a diagram of one method of connecting six coverslips 18 and showing how each group of six is scored along line 80 for easy separation.

Another embodiment of tray 14 is one in which the bottom of each well 24 is made of a soft or pliable material. The purpose of the soft bottom is that it becomes easy to remove air bubbles which may be trapped under a slide 70. By pushing on the soft bottom of a well 24 one can easily move air bubbles to a region away from the region of the tissue sample. In this embodiment it may be especially desirable to make the wells 24 from a transparent material to make it simpler to observe any air bubbles which may be present. Aside from the well 24 bottoms it is best to manufacture the remainder of the tray 14 from a stiff material for ease of handling. The advantage of the soft bottom is that the necessary volume of reagent solution to be added to a well becomes flexible.

Another embodiment of tray 14 is a notch or channel 45 on the top of well boundary 44 and a channel 47 in the bottom of well boundary 44. A tubing 146 is on the outside of the bottom well boundary 44. Tubing 146 includes a valve 149. This embodiment allows the slideholder 1 plus slides 70 to be placed onto wells 24 of tray 14 prior to adding solution to the wells 24. The solution may be added later through tubing 146. The solution enters wells 24 from tubing 146 via channel 47. Air that is in wells 24 escapes through notch or channel 45 as solution is added.

Figure 7E:
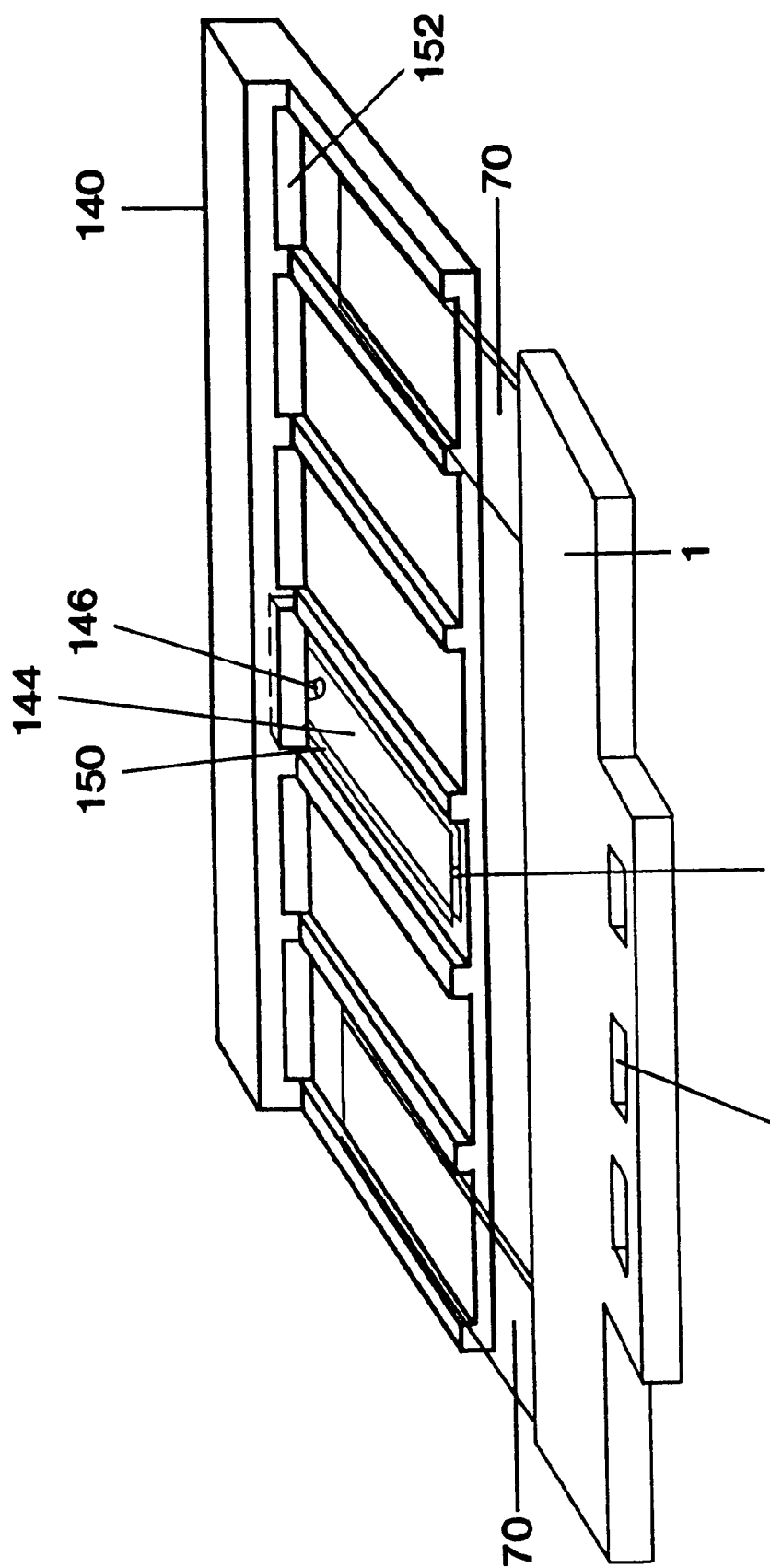
FIG. 7E shows a bottom elevational view of special multiple chamber coverslip 140. Slides 70 which are held by slideholder 1 are inserted into slots 152 of coverslip 140.

A different embodiment of the invention is one in which no tray 14 is used, rather the tissue samples are mounted onto slides 70, the slides 70 are left face up, and a special multichamber coverslip 140 is placed on top of the slides 70. This is illustrated in FIGS. 7A and 7B. It is preferred that the slides 70 are first placed into a slideholder 1. The special coverslip 140 actually consists of three or six conjoined coverslips 142 properly spaced so as to align with slides 70 which are in a slideholder 1. A further feature of this special coverslip 140 is that it comprises "soft tops" 144 rather than simply being a hard coverslip. The purpose of the soft top 144 is to be able to push any trapped air bubbles to a region away from the tissue sample. Again, it is desirable to manufacture these from a transparent material such that it is easier to observe trapped air bubbles. Another feature is that these special coverslips 140 may have a raised region 150 toward the edges of each coverslip 142 which can trap air which is pushed into the region 150 and thus trap air bubbles which have been pushed to the edges and thereby prevent the air bubble from returning to the area of the slide 70 on which the tissue sample is mounted. FIGS. 7A–E illustrates this special multichamber coverslip. The soft top 144 is in the region between the raised region 15. Although soft top 144 is illustrated as a rectangular area in FIG. 7B it can be any other desired shape such as an oval or circle. Aside from the soft top 144 the rest of the special coverslip 140 is made of a stiff material. Ridges 160 are present to easily align the coverslip 140 properly onto slides 70.

Another feature which may be included in this multichamber coverslip 140 is to include slots 152 into which the ends of slides 70 may be inserted. Thus one end of each slide 70 will be inserted into slideholder 1 and the opposite end will be inserted into a slot 152 of coverslip 140. This slot 152 will help to align and hold the coverslip 140 on slides 70 during transportation of slideholder 1, slides 70 and coverslip 140.

An additional feature which can be included in this embodiment is to include a tubing 146 on one side of the coverslip 140 and a very small hole 148 on the other side. The tubing 146 is connected to a valve 149 through which reagents can be added and which can be closed to seal the tubing 146. This feature allows the multichamber coverslip 140 to be placed onto the slides 70 of the slideholder 1 prior to addition of solutions. The solutions are then added through tubing 146. The air in the chamber can escape through the very small hole 148.

A variation of this last embodiment is a specially designed coverslip 170 to be used for in situ PCR. This is illustrated in FIGS. 8A and 8B. FIG. 8A is an elevational view which shows three coverslips joined together. This coverslip 170 has a "soft top" 174, e.g., polyethylene or low density polyethylene, which allows for expansion and contraction of the PCR reaction fluid on the tissue sample during the temperature cycling. The soft top region 174 is surrounded by a stiff region 176 which is outside the region of the tissue sample. In its most simple form, the PCR solution is placed onto the tissue sample on a slide 70 and the coverslip 170 is placed onto the slide 70 such that the soft top region 174 is over the tissue. Stiff region 176 may be adhesive backed and will stick onto the slide 70 and seal the coverslip 170 onto the slide 70 and prevent evaporation. This soft top bubble type incubation coverslip works like a balloon. When the temperature increases, it will expand and when the temperature decreases it will shrink in response to the expansion and contraction of the liquid within the well. The pressure inside the well chamber will be significantly reduced by this soft top design. This low pressure may reduce or eliminate the expansion and contraction of the solution and allow mainly only an up and down movement of the solution thereby restraining the movement of newly formed products from their original sites. Consequently, this inhibits the diffusion of PCR products and increases the signal at the original sites.

The soft top bubble type incubation coverslip looks like an umbrella or a tent with a high fixed frame and shape to prevent the soft top coverslip from touching the tissue on the slide. This is illustrated in FIG. 8B. However, the soft top has enough space to expand and contract without generating a high pressure. This design advantage allows the use of regular plastic material and eliminates the need for using steel clips and a silicone disc to prevent leaking.

As illustrated in FIG. 8A one can join three coverslips 170 together to simultaneously process positive and negative controls along with the experimental sample. These may be designed to cover three tissue samples all mounted onto a single slide if desired. By placing all three samples on a single slide the PCR is more consistent across all three samples.

PCR coverslip 170 may be modified to perform hot start PCR. This is illustrated in FIG. 8B. For this the soft top 174 is modified to be made of a stiffer plastic material, e.g., polypropylene, and to include a short tube 180 through which reagents may be added. The coverslip is placed onto the slide 70 with the soft top covering the tissue sample. The first portion of the PCR solution is pipetted through the tube 180. The slide is placed onto a thermal cycler and heated. Following the initial heating the remaining reagents are added by pipetting through tube 180. Tube 180 may then be sealed with a heat sealer. This prevents evaporation of fluid during the cycling steps.

EXAMPLES

In each example a tissue sample is first mounted onto a microscope slide 70 and then assayed. Surgical and autopsy human tissue samples from various organs (lymph node, liver, kidney, lung, breast, skin, prostate) were routinely fixed in 10% neutral buffered formalin, processed overnight on a tissue processor, and embedded in paraffin. Serial sections are cut at 4–5 microns and mounted onto Probe-On-Plus Slides (#15-188-52; Fisher Scientific) and dried overnight at room temperature. Slides 70 are then inserted into a reusable slideholder 1. At this point all the slides 70 in a single holder 1 (up to six slides) can be handled simultaneously. The slides 70 are deparaffinized by placing the slides 70 in a staining dish with four changes of xylene for 5 minutes each, two treatments of 100% ethanol for 1 minute each and two treatments of 95% ethanol for 1 minute each. The deparaffinized tissue section slides 70 are cleared and washed with deionized water.

The present invention is further detailed in the following Examples, which are offered by way of illustration and are not intended to limit the invention in any manner. Standard techniques well known in the art or the techniques specifically described below are utilized.

Example 1

Hematoxylin and Eosin (H & E)

Hematoxylin and eosin is the most common staining procedure used in pathology. Every case must have H & E staining for making a pathologic diagnosis. Deparaffinized tissue section slides 70 which are in slideholders 1 are placed vertically into a staining dish with 500 mL of hematoxylin solution for two minutes followed by washing with running tap water in a staining dish for five minutes. The slides are placed in 95% ethyl alcohol for one minute and counterstained in eosin-phloxine solution for two minutes. The samples are dehydrated and cleared using two changes each of 95% ethyl alcohol, absolute ethyl alcohol, and xylene for two minutes each.

Coverslips are attached as follows: Place one drop of Cytoseal 60 or premount on the tissue section side of each slide 70 with the slides 70 still attached to the slideholder 1. Place coverslips 18 onto each slide 70. Although this may be done one by one, it is more efficient to use a specially designed coverslip 76 which is actually six (or three) conjoined coverslips 18 properly spaced to align with six (or three) slides 70. Using this special coverslip 76, up to six individual coverslips 18 are effectively aligned and placed onto slides 70 simultaneously. The coverslips 18 are easily separated from the plastic strip 78 holding them together simply by bending the coverslip 76 which is prescored to allow the strip 78 to snap apart from the coverslips 18 which remain bound to the slides 70. At this point the slides 70 may be removed from the slideholder 1 to be handled individually, or they may be left attached to the slideholder 1 for ease of transportation.

Example 2

Immunocytochemistry

In this Example a tissue sample is treated with antibodies (primary and secondary), treated for chromogen color development, and finally counterstained.

A. Proteolytic pretreatment of mounted tissue samples

It is well known in the art that when using certain antibodies for immunocytochemical staining it is necessary to pretreat the formalin fixed tissue section with proteolytic enzymes such as 0.4% pepsin, pH 2.0. When this is necessary the following steps may be utilized. A few drops (150–200 μL) of the proteolytic digestion solution are placed on each well 24 of the 3 or 6 well tray 14. The tissue side of the slides 70 is faced down on the wells 24. The slideholder 1 with the slides 70 should be slowly laid down and placed on the wells 24 of the tray 14. No air bubbles should remain between the tissue side of the slides 70 and the solution in the wells 24 of the tray 14. The slides 70, slideholder 1 and tray 14 with solution are incubated for 15 minutes at 40° C.

If many samples are being processed at one time it is more efficient to forgo use of the tray 14 during this proteolytic pretreatment step. The slides 70 are still placed into slideholders 1 six to a holder 1. The slideholders 1 and slides 70 are then placed vertically into a staining dish with 500 mL of the proteolytic digestion solution (which may be reused) and incubated for 20 minutes at 40° C. in a water bath. Up to twenty slideholders 1 (120 slides) may be simultaneously placed into the staining dish for this pretreatment step.

Some antibodies require that the tissue section be pretreated with microwave antigen retrieval. Slideholders 1 (up to 20) with slides 70 are vertically placed into a staining dish with 500 mL of 0.01 M citrate buffer, the staining dish is placed in the center of a microwave oven, and the oven is turned to high power (800–850 Watts) for 7–8 minutes bringing the solution to a rapid boil. The oven is turned off, the power level is reset to 400 Watts, and the oven is turned on again to heat the solution for 7–8 minutes.

After proteolytic digestion and microwave treatment the tissue sections are washed in the staining dish with three 500 mL changes of phosphate buffered saline (PBS).

B. Treatment of tissue sections with goat and horse serum

All slides 70, whether or not proteolytically digested and microwave treated, are incubated with 5% mixed normal goat and horse serum for 20–30 minutes at room temperature. Each well 24 of a tray 14 is filled (approximately 150–200 μL) with mixed normal goat and horse serum. The tissue side of the slides 70 is placed down on the wells 24 to contact the serum. The slideholder 1 should be slowly laid down so as to avoid trapping any air between the slides 70 and the wells 24. Again, if many samples are being processed at one time, it is more efficient to perform this step as a batch by placing up to 20 slideholders 1 vertically into a staining dish with 500 mL of 5% mixed normal goat and horse serum for 20–30 minutes.

C. Application of the primary antisera or antibodies

Following incubation with the serum, the slideholder 1 and slides 70 as well as the tray 14 are put into a staining dish with PBS. The tray 14 is separated from the slideholder 1 and both are washed once with PBS. The washed tray 14 may be reused for the next step. Prediluted primary antisera or antibodies (approximately 150–200 μL) are applied to each well 24 of the tray 14. The washed slides 70, still in the slideholder 1, are placed tissue side down onto the wells 24. As always care must be taken to avoid trapping bubbles between the slide 70 and the reagent solution in the wells 24. The samples are incubated with the antisera or antibodies for 2–4 hours at room temperature or incubated in a humidity chamber at 40° C. for 2 hours or may be incubated in a humidity chamber at room temperature overnight. After incubation the slideholder 1 and attached slides 70 are removed from the tray 14 and are washed in a staining dish with PBS three times.

D. Application of the secondary antibody

Prediluted secondary antibody (approximately 150–200 μL) is applied into each well 24 of a new tray 14. The slides 70 in the slideholder 1 are placed onto the wells 24 tissue side down being careful to avoid bubbles. This is incubated for 30 minutes at 40° C. in a humidity chamber. After incubation the slideholders 1 and attached slides 70 are removed from the tray 14 and washed in a staining dish with three changes of PBS.

E. Treatment for removal of endogenous peroxidase activity

All slideholders 1 with attached slides 70 are placed into a staining dish with 500 mL of PBS with 3% hydrogen peroxide and 0.1% sodium azide, and incubated at room temperature for 15 minutes. After incubation with the hydrogen peroxide PBS the slideholders 1 and attached slides 70 are washed in a staining dish with three changes of PBS.

F. Application of the ABC complex "ELITE"

The ABC complex (Vector Laboratories Inc., Burlingame, Calif.) is diluted to its working dilution using PBS. The working dilution (approximately 150–200 μL) is applied to each well 24 of a new tray 14. The slides 70 with attached slideholders 1 are carefully placed tissue side down onto the trays 14 so that no air bubbles are trapped between the solution and the slides 70. The slides 70 and trays 114 with ABC solution are incubated in the humidity chamber at 40° C. for 30 minutes. After incubation the slideholders 1 with attached slides 70 are removed from the trays 14 and washed in a staining dish with 3 changes of PBS.

G. Chromogen Color development using diaminobenzidine (DAB)

DAB solution is prepared by adding 100 mg DAB to 100 mL PBS and adding 50 μL of 30% $H_2O_2$. Approximately 150–200 μL of the DAB solution is added to each well 24 of a new tray 114 to completely fill each well 24. The slides 70 with attached slideholders 1 are placed tissue side down onto the wells 24 being careful to avoid trapping air bubbles. Color development can be monitored by viewing the slideholders 1 and trays 14 with DAB under a microscope. A colored precipitate will form at the site of positive cells. Color begins to appear after 2–5 minutes, usually reaching sufficient development within 10 minutes, but a 20–30 minute incubation may be necessary for weakly stained samples. To stop development, all slideholders 1 with slides 70 are removed from the trays 14 and washed in a staining dish with three changes of deionized water.

H. Counterstaining

Slideholders 1 and attached slides 70 are immersed in Harris's hematoxylin for 10–50 seconds and washed by dipping into deionized water for three changes. Then all the slides 70 are immersed in 0.2% ammonium hydroxide solution for 30 seconds and washed by dipping in deionized water for 3 changes. The slides 70 are dipped into 95% ethanol for two changes of 2 minutes each, followed by dipping into 100% ethanol for 2 changes of 2 minutes each, and finally the slides 70 are cleared by dipping into two changes of xylene for 2 minutes each.

I. Attachment of the Coverslip

Place 1 drop of Cytoseal 60 or premount on the tissue section side of each slide 70 with the slides 70 still attached to the slideholder 1. Place coverslips 18 onto each slide 70. Although this may be done one by one, it is more efficient to use a specially designed coverslip 76 which is actually six (or three) conjoined coverslips 18 properly spaced to align with six (or three) slides 70. Using this special coverslip 76, up to 6 individual coverslips 18 are effectively aligned and placed onto slides 70 simultaneously. The coverslips 18 are easily separated from the plastic strip 78 holding them together simply by bending the coverslip 76 which is prescored to allow the strip 78 to snap apart from the coverslips 18 which remain bound to the slides 70. At this point the slides 70 may be removed from the slideholder 1 to be handled individually, or they may be left attached to the slideholder 1 for ease of transportation.

FIGS. 10–12 show the results of a study comparing the use of the present invention with staining methods simply using the standard manual method of dropping reagents onto the surface of a slide-mounted tissue sample and leaving the reagents open to the atmosphere for incubation. The Figures show that the results obtained with the two methods are extremely comparable with the results obtained using the present invention being at least as good as, and apparently better than, the results obtained using the traditional method. The present invention however allowed these results to be obtained with less work and with the use of smaller amounts of reagents.

Comparing the two methods, the background staining is significantly reduced by using the present invention, especially when using polyclonal antibodies (anti-kappa light chain antibodies and anti-lambda light chain antibodies). The invention significantly improves the staining results by reducing the background. Background is partially due to free FC fragments which precipitate by gravity and bind nonspecifically to the tissue. The present method inverts the slide such that the tissue is above the solution and therefore free FC fragments cannot precipitate by gravity onto the tissue.

Example 3

In Situ Hybridization

In this example tissue samples are mounted onto slides 70, hybridized with biotin or digoxigenin labeled probes and reacted with anti-biotin or anti-digoxigenin antibody. The samples are then stained.

A. Preparation and mounting of tissue sample

A tissue sample is prepared as described above but with extra measures to prevent nucleic acid degradation. A tissue sample is fixed in 10% neutral buffered formalin, processed overnight on a tissue processor, embedded in paraffin, cut into serial sections of 4–5 microns, mounted onto Probe-On-Plus Slides (#15-188-52; Fisher Scientific), and dried overnight at room temperature. The slides 70 are inserted into a slideholder 1 and are deparaffinized by placing into a staining dish. The slides 70 are treated with four changes of xylene for 5 minutes each, two changes of 100% ethanol for 1 minute each and two changes of 95% ethanol for 1 minute each. The deparaffinized tissue section slides are then cleared and washed with deionized water with RNase Block (BioGenex, San Damon, Calif.).

B. Proteinase K treatment of the mounted tissue samples

Approximately 150–200 μL of freshly diluted proteinase K solution is placed into each well 24 of a tray 14 to completely fill each well 24. The microscope slides 70 (still in the slideholder 1) are placed onto the wells 24 with the tissue side down. The slides 70 are placed onto the wells 24 carefully so as to avoid the presence of air bubbles between the solution in the wells 24 and the slide 70. This is incubated for 15 minutes at room temperature.

After digestion, the slideholders 1 with slides 70 attached are removed from the tray 14 and washed in a staining dish with 500 mL of PBS with RNase Block for 5 minutes. The tissue section slides 70 are dehydrated by immersing in a staining dish serially in the following solutions: 500 mL distilled water plus RNase Block for 10 seconds, 500 mL 50% ethanol plus RNase Block for 10 seconds, 500 mL of 95% ethanol for 10 seconds, and 500 mL 100% ethanol for 10 seconds. The slides 70 are dried at room temperature for 5 minutes.

C. Hybridization with biotinylated or digoxigenin labeled probes

Trays 14 with shallow wells 24 (0.02–0.08 mm in depth) may be used here to conserve materials. Hybridization solution containing a biotinylated or digoxigenin labeled oligonucleotide probe is placed into each well 24 of a tray 14. Enough solution is added to each well 24 to completely fill the well 24. This requires approximately 50–100 μL of solution. The slides 70 are placed on top of the wells 24 (3 or 6 at a time still attached to the slideholders 1) being careful not to trap any air bubbles. The trays 14 plus slideholders 1 and slides 70 are placed in an oven or on a heating block at 95° C. for 8–10 minutes to denature the nucleic acids. This step eliminates hair-pin loops or folding back of mRNA sequences. After the denaturation step, the slides 70 are incubated in a humidity chamber at 45° C. overnight. Following the hybridization step, the slides 70 are washed by removing the slideholders 1 with attached slides 70 from the trays 14 and washing the slides 70 in a staining dish with 2×SSC (standard saline citrate) at 37° C. for 5 minutes followed by a wash with 1×SSC at 37° C. for 5 minutes. This is followed by a 30 minute wash in 0.2×SSC at 60° C. Finally the slides 70 are washed with 2 changes of PBS for 2–5 minutes each.

D. Signal detection

The slideholders 1 with attached slides 70 are placed vertically into a staining dish with 500 mL of 5% mixed normal goat and horse serum at room temperature for 20 minutes. Prediluted mouse anti-biotin or mouse anti-digoxigenin antibody (150–200 μL) is applied to each well 24 of a new tray 14. The slides 70 are placed onto the wells 24 of the tray 14 taking care to avoid trapping bubbles. The slides 70 and trays 14 with antibody are incubated in a humidity chamber at 40° C. for 2 hours.

After incubation with the anti-biotin or anti-digoxigenin antibody, the slideholders 1 with slides 70 are removed from the trays 14 and washed in a staining dish with three changes of PBS.

E. Application of the secondary antibody

Prediluted secondary antibody (approximately 150–200 µL) is applied into each well 24 of a new tray 14. The slides 70 in the slideholder 1 are placed onto the wells 24 tissue side down being careful to avoid bubbles. This is incubated for 30 minutes at 40° C. in a humidity chamber. After incubation the slideholders 1 and attached slides 70 are removed from the tray 14 and washed in a staining dish with three changes of PBS.

F. Treatment for removal of endogenous peroxidase activity

All slideholders 1 with attached slides 70 are placed into a staining dish with 500 mL of PBS with 3% hydrogen peroxide and 0.1% sodium azide, and incubated at room temperature for 15 minutes. After incubation with the hydrogen peroxide PBS the slideholders 1 and attached slides 70 are washed in a staining dish with three changes of PBS.

G. Application of the ABC complex "ELITE"

The ABC complex is diluted to its working dilution using PBS. The working dilution (approximately 150–200 µL) is applied to each well 24 of a new tray T4. The slides 70 with attached slideholders 1 are carefully placed tissue side down onto the trays 14 so that no air bubbles are trapped between the solution and the slides 70. The slides 70 and trays 14 with ABC solution are incubated in the humidity chamber at 40° C. for 30 minutes. After incubation the slideholders 1 with attached slides 70 are removed from the trays 14 and washed in a staining dish with 3 changes of PBS.

H. Chromogen color development using diaminobenzidine (DAB)

DAB solution is prepared by adding 100 mg DAB to 100 mL PBS and adding 50 µL of 30% $H_2O_2$. Approximately 150–200 µL of the DAB solution is added to each well 24 of a new tray 14 to completely fill each well 24. The slides 70 with attached slideholders 1 are placed tissue side down onto the wells 24 being careful to avoid trapping air bubbles. Color development can be monitored by viewing the slideholders 1 and trays 14 with DAB under a microscope. A colored precipitate will form at the site of positive cells. Color begins to appear after 2–5 minutes, usually reaching sufficient development within 10 minutes, but a 20–30 minute incubation may be necessary for weakly stained samples. To stop development, all slideholders 1 with slides 70 are removed from the trays 14 and washed in a staining dish with three changes of deionized water.

I. Counterstaining

Slideholders 1 and attached slides 70 are immersed in Harris's hematoxylin for 10–50 seconds and washed by dipping into deionized water for three changes. All the slides 70 are immersed in 0.2% ammonium hydroxide solution for 30 seconds and washed by dipping in deionized water for 3 changes. The slides 70 are then dipped into 95% ethanol for two changes of 2 minutes each, followed by dipping into 100% ethanol for 2 changes of 2 minutes each, and finally the slides 70 are cleared by dipping into two changes of xylene for 2 minutes each.

J. Coverslipping

Place 1 drop of Cytoseal 60 or premount on the tissue section side of each slide 70 with the slides 70 still attached to the slideholder 1. Place coverslips 18 onto each slide 70. Although this may be done one by one, it is more efficient to use a specially designed coverslip 76 which is actually six (or three) conjoined coverslips 18 properly spaced to all line up with six (or three) slides 70. Using this special coverslip 76, up to 6 individual coverslips 18 are effectively aligned and placed onto slides 70 simultaneously. The coverslips 18 are easily separated from the plastic strip 70 holding them together simply by bending the strip 78 which is prescored to allow the strip 78 to snap apart from the coverslips 18 which remain bound to the slides 70. At this point the slides 70 may be removed from the slideholder 1 to be handled individually, or they may be left attached to the slideholder 1 for ease of transportation.

Example 4

PCR In Situ Hybridization

Polymerase chain reaction (PCR) was developed as an in vitro method for amplifying small amounts of specific pieces of nucleic acids. This was later adapted to in situ studies so that there was amplification of nucleic acid within tissue sections. The apparatus of the present invention is suited to performing these in situ PCRs. An example of a PCR in situ hybridization protocol is given in G. J. Nuovo *J. Histotechnology* 17:235–242 (1994).

A. In situ PCR

Serial tissue sections are cut at 4–5 microns thickness, mounted onto Probe-On-Plus slides 70, and dried overnight at room temperature. The mounted tissue sections are deparaffinized and digested with pepsin at 40° C. for 15–90 minutes depending on the length of time of fixation in formalin. The pepsin is inactivated by washing the slides 70 in diethylpyrocarbonate (DEPC) treated water for one minute followed by a one minute wash in 100% ethanol. The slides 70 are then air dried.

Polymerase chain reaction solutions are made according to any standard procedure. See, e.g., K. B. Mullis et al., U.S. Pat. No. 4,800,159. Combine buffer, 5' and 3' primers, water, Taq polymerase (AmpliTaq, Perkin Elmer) (or other thermophilic polymerase) and Self-Seal Reagent (MJ Research, Inc.) in a total volume of 20–50 µL. Apply the 20–50 µL of solution to a well 24 of a specially designed in situ PCR aluminum tray 14. The trays 14 to be used in Examples 1 and 2 are preferably made of a disposable plastic material, but the trays 14 used for PCR studies must be capable of being cycled through a series of temperatures which may reach 95–100° C. Therefore it is necessary for such trays 14 to be heat resistant (i.e., they should not melt or otherwise be destroyed by high temperatures) and also to be good conductors of heat. Aluminum is a preferred material from which to manufacture these trays 14. These aluminum trays 14 have wells 24 which are 0.005–0.03 mm in depth and hold approximately 20–50 µL of solution.

After completely filling each well 24 of the aluminum tray 14, the slideholder 1 and attached slides 70 are placed on top of the tray 14 with the tissue section facing down so as to contact the solution in the well 24 upon which it is placed. Care must be taken to avoid air bubbles being present between the solution and the slide. The slideholder 1, slides 70 and aluminum tray 14 are then placed onto a block of a thermal cycler at 95° C. for 3–5 minutes to denature the nucleic acids in the tissue. Twenty to thirty cycles are then performed cycling between 60° C. for 2 minutes and 94° C. for 1 minute.

Following the cycling steps, the slideholder 1, slides 70 and aluminum tray 14 are placed vertically into a staining dish with 2×SSC at 37° C. for 5 minutes. The slideholder 1 is removed from the aluminum tray 14 and washed with 0.5–1×SSC at 37–60° C. for 10–30 minutes (depending upon background). In situ hybridization is performed as described in Example 2 using a biotinylated or digoxigenin labeled probe chosen internal to the primers.

B. Reverse Transcriptase In Situ PCR

Serial tissue sections are cut at 4–5 microns thickness, mounted onto Probe-On-Plus slides 70, and dried overnight at room temperature. An important aspect of the RT in situ PCR is that both negative and positive controls be performed and it is preferred that these be performed on the same glass slide. The positive control omits the DNAse digestion step and should generate an intense nuclear signal from target specific amplification, DNA repair and mispriming. The negative control uses a DNAse treatment plus primers that do not correspond to a target in the cells. The test sample undergoes DNAse treatment but uses primers specific to the desired target nucleic acid. The mounted tissue sections are deparaffinized and digested with pepsin at 40° C. for 15–90 minutes depending on the length of time of fixation in formalin. The pepsin is inactivated by washing the slides 70 in diethylpyrocarbonate (DEPC) treated water for one minute followed by a one minute wash in 100% ethanol. The slides 70 are then air dried.

Digest two of the three mounted tissue sections with RNase-free DNAse by filling each well 24 of a plastic tray 14 (requiring approximately 150–200 $\mu$L) with prediluted RNase-free DNAse and placing the slides 70 (in the slideholder 1) tissue side down on top of the well 24 being careful that air bubbles are not trapped and that contact is made between the solution in the well 24 and the tissue sample. Incubate overnight at 37° C. Inactivate the RNase-free DNAse with a 1 minute wash in DEPC water and a 1 minute wash in 100% ethanol. Let the slides 70 air dry.

The reverse transcription is performed using the EZ RT PCR system (Perkin Elmer). The RT/amplifying (RT-PCR) solution contains EZ rTth buffer, 200 $\mu$M each of dATP, dCTP, dGTP and dTTP, 400 $\mu$g/mL bovine serum albumin, 40 Units RNasin, 0.8 $\mu$M of 5' and 3' primers, 2.5 mM manganese chloride, 5 Units of rTth, and 2× concentrated Self-Seal Reagent (MJ Research, Inc.). Twenty to fifty $\mu$L of the RT-PCR mixture is placed into each of three wells 24 in a specially designed in situ PCR aluminum tray 14 (the depth of the wells 24 is approximately 0.005–0.03 mm) to fill the wells 24. The slides 70 are carefully placed onto the wells 24 with the tissue being placed in contact with the solution inside of the well 24. The slides 70, slideholder 1 and aluminum tray 14 are placed onto a block of a thermal cycler at 65° C. for 30 minutes followed by a denaturation step at 94° C. for 3 minutes. Twenty to 30 cycles are performed, each cycle being 60° C. for 2 minutes followed by 94° C. for 1 minute.

Following the cycling steps, the slideholder 1, slides 70 and aluminum tray 14 are placed vertically into a staining dish with 2×SSC at 37° C. for 5 minutes. The slideholder 1 is separated from the aluminum tray 14 and washed with 0.5–1×SSC at 37–60° C. for 10–30 minutes (depending upon background). In situ hybridization is performed as described in Example 2 using a biotinylated or digoxigenin labeled probe chosen internal to the primers.

The above Examples are only exemplary and not meant to be limiting of the techniques which may be performed using the apparatus which is defined by the present invention. The stated measurements are also exemplary and not meant to be limiting as it will be obvious to one of skill in the art that the exact measurements are not critical and can be varied to still yield successful results. Those skilled in the art will readily perceive other applications for the present invention.

What is claimed is:

1. A multiwell tray for processing samples mounted onto microscope slides, said tray comprising a base and wells for holding reagents surrounded by boundaries within said base and wherein reagents placed into said wells can contact said microscope slides when said microscope slides are placed on top of said wells, and further comprising tubing opening to each well through a first port in said boundaries and wherein said boundaries further include a second port through which air can vent when said wells are covered by slides and solution is added to said wells through said tubing.

2. The tray of claim 1 wherein said wells are elevated above said base.

3. The tray of claim 1 wherein said boundaries have flat surfaces wherein all flat surfaces are at equal heights thereby allowing all slides simultaneously to lay flat on the surfaces.

4. The tray of claim 1 wherein the number of wells is chosen from the group consisting of: one well wide enough to accommodate 6 microscope slides side by side, two wells each of which is wide enough to accommodate 3 microscope slides side by side, and 6 wells each of which is wide enough to accommodate only a single microscope slide.

5. The tray of claim 1 wherein said tubing comprises a valve.

6. The tray of claim 1 wherein said tray comprises a trough within which a slideholder may be placed.

7. The tray of claim 1 wherein said tray is aluminum.

8. The tray of claim 1 wherein said tray is color coded.

9. The multiwell tray of claim 1 in combination with a microscope slide placed on top of said tray.

10. The multiwell tray of claim 1 in combination with a microscope slide placed on top of said tray wherein said microscope slide comprises a sample to be assayed and wherein said sample contacts a reagent in said well.

11. The tray of claim 1 wherein said wells have a bottom comprising a soft material.

12. The tray of claim 11 wherein said wells are transparent.

13. The tray of claim 1 further comprising means to hold slides flat against said boundaries.

14. The tray of claim 13 wherein said means is a hook.

15. The tray of claim 1 wherein said wells are separated by troughs.

16. The tray of claim 15 in combination with a microscope slide placed on top of said tray.

17. The multiwell tray of claim 15 in combination with a microscope slide placed on top of said tray wherein said microscope slide comprises a sample to be assayed and wherein said sample contacts a reagent in said well.

18. The tray of claim 15 wherein each of said wells holds anywhere from 50 to 300 $\mu$L.

* * * * *